United States Patent [19]
Lange et al.

[11] Patent Number: 5,939,539
[45] Date of Patent: Aug. 17, 1999

[54] GA 20-OXIDASE GENE SEQUENCES

[75] Inventors: Theodor Lange; Jan E. Graebe, both of Göttingen, Germany; Peter Hedden; Andrew Phillips, both of Bristol, United Kingdom

[73] Assignee: Long Ashton Research Station, Long Ashton, United Kingdom

[21] Appl. No.: 08/553,367

[22] PCT Filed: May 24, 1994

[86] PCT No.: PCT/EP94/01664

§ 371 Date: Nov. 27, 1995

§ 102(e) Date: Nov. 27, 1995

[87] PCT Pub. No.: WO94/28141

PCT Pub. Date: Dec. 8, 1994

[30] Foreign Application Priority Data

May 28, 1993 [GB] United Kingdom ............... 9311147

[51] Int. Cl.[6] .............. C07H 21/04; C12N 1/21; C12N 15/63; C12Q 1/68
[52] U.S. Cl. .......... 536/23.2; 536/23.1; 536/23.4; 536/23.6; 435/6; 435/69.1; 435/252.3; 435/320.1; 435/410
[58] Field of Search ................ 536/23.2, 23.4, 536/23.6, 23.1; 435/69.1, 6, 252.3, 410, 320.1

[56] References Cited

U.S. PATENT DOCUMENTS

5,210,189   5/1993   Murata .

FOREIGN PATENT DOCUMENTS

0 388 186 A1   9/1990   European Pat. Off. .

OTHER PUBLICATIONS

Gilmour et al., "Partial Purification of Gibberellin Oxidases from Spinach Leaves[1]", Plant Physiol. vol. 85, pp. 87–90, 1987.

Graebe et al. "The Relationship of Different Gibberellin Biosynthetic Pathways in *Cucurbita maxima* Endosperm and Embryos and the Purification of a C–20 Oxidase from the Endosperm", Gibberellins; Symposium, Tokyo, Japan, Jul. 20–23, Takahashi et al. (eds), pp. 51–61, 1989.

Kamiya et al., "Conversion of Gibberellin $A_{20}$ to Gibberellins $A_1$ and $A_5$ in A Cell–Free System from *Phaseolus vulgaris*", Planta vol. 162, 154–158, 1984.

Lange et al., "The Partial Purification and Characterization of A Gibberellin C–20 hydroxylase from Immature *Pisum sativum* L. Seeds", Planta vol. 179, pp. 211–221, 1989.

Lange et al., "Biosynthesis of 12α–and 13–hydroxylated Gibberellins in A Cell–Free System from *Cucurbita maxima* endosperm and the Identification of New Endogenous Gibberellins", Planta, vol. 189, pp. 340–349, 1993.

Plant Physiology Supplement, vol. 89, No. 4, Apr. 1989, Wilson, T.M., et al., "Purification of a Gibberellins 53–oxidase from Spinach", see abstract 633.

Basic Methods in Molecular Biology 1986 Davis, Dibner and Battey eds, Elsevier, New York Chapter 14 pp. 194–215.

1992 New England Biolabs Catalog, p. 119.

Murray and Thompson, Nucleic Acid Research 8:4321, 1980.

Xu et al. PNAS 92:6640 1995.

*Primary Examiner*—Paula K. Hutzell
*Assistant Examiner*—Nancy A. Johnson
*Attorney, Agent, or Firm*—Wenderoth, Lind & Ponack, L.L.P.

[57] ABSTRACT

The invention relates to the molecular cloning and expression of a gibberelin (GA) 20-oxidase gene and its use, for example in transgenic plants. Aspects of the invention include recombinant DNA which encodes a polypeptide exhibiting GA 20-oxidase activity, a recombinant polypeptide exhibiting GA 20-oxidase activity, and transgenic plants which express a GA 20-oxidase gene or reverse GA 20-oxidase sequences.

34 Claims, No Drawings

GA 20-OXIDASE GENE SEQUENCES

BACKGROUND OF THE INVENTION

1. Field of the Invention

This invention relates to the regulation of plant growth, and more particularly to the molecular cloning and expression of a gibberellin 20-oxidase gene and its use, for example in transgenic plants.

2. Description of the Related Art

Chemical compounds for control of plant growth have been in commercial use for many years. Many of these compounds act by inhibiting various steps in the biosynthesis of gibberellins (GAs). GAs form a large group of diterpenoid natural products, some members of which function as hormones in plants, controlling many aspects of development, including, for example, shoot elongation. Among the groups of compounds which inhibit GA biosynthesis in higher plants are quaternary ammonium and phosphonium compounds, compounds with a nitrogen-containing heterocycle, and acylcyclohexane-diones. However, the use of such chemicals involves several problems. It is, for example, difficult to apply the chemicals to plants in the appropriate quantities, or to select plant organs, without the chemicals spreading to other plants or animal life. There is a risk of persistence which can make it difficult to grow other crops subsequently to treated crops. A problem addressed by the present invention is therefore to avoid the use of such chemicals. This problem can be solved within this application by providing means for plant growth control at the plant gene level.

The later steps of the GA biosynthetic pathway are catalysed by soluble 2-oxoglutarate-dependent dioxygenases, several of which have been proposed as regulatory enzymes in the biosynthesis of the physiologically important $C_{19}$ compound, $GA_1$. For example, the activity of the GA 20-oxidase is enhanced by long days in certain photoperiod-sensitive plants and is down-regulated as a consequence of $GA_1$ action in several species.

SUMMARY OF THE INVENTION

According to the invention, there is provided a DNA sequence which encodes a polypeptide exhibiting GA 20-oxidase activity. This disclosure is the first example of the molecular cloning of a GA:2-oxoglutarate dioxygenase. The enzyme GA 20-oxidase is also known as a 20-hydroxylase or C-20 oxidase, as it catalyses oxidation reactions at the C-20 carbon atom of the GA structure. It is a dioxygenase, as oxoglutarate is simultaneously oxidised.

DESCRIPTION OF THE PREFERRED EMBODIMENTS

As demonstrated in the Examples the DNA sequence of the present invention encodes GA 20-oxidase capable of acting essentially on one or more of the following substrates: $GA_{12}$, $GA_{53}$, $GA_{15}$ (open or closed lactone), $GA_{44}$ (open or closed lactone), $GA_{24}$, $GA_{19}$ and $GA_{23}$ among others.

The present invention thus further relates to a DNA sequence encoding a polypeptide exhibiting GA 20-oxidase activity, in which the polypeptide exhibiting GA 20-oxidase activity is capable of acting essentially on one or more of the following substrates: $GA_{12}$, $GA_{53}$, $GA_{15}$ (open or closed lactone), $GA_{44}$ (open or closed lactone), $GA_{24}$, $GA_{19}$ and $GA_{23}$.

The DNA sequence of the invention may encode a GA 20-oxidase from, in principle, any plants or fungi, but preferably from monocotyledonous and dicotyledonous plants, and more preferably from dicotyledonous plants. A particularly suitable source is plants of the family Cucurbitaceae, such as *C. maxima*, of which the immature seeds are a convenient source. A further suitable source is plants of the family Cruciferae, such as *Arabidopsis thaliana*, of which shoot material is a convenient source.

A preferred embodiment of the invention is therefore a DNA sequence which encodes a GA 20-oxidase obtainable from plants or fungi, preferably from monocotyledonous and dicotyledonous plants respectively, more preferably from dicotyledonous plants and most preferably from plants of the family Cucurbitaceae and Cruciferae respectively, such as *C. maxima* and *Arabidopsis thaliana*, or a protein having substantial homology thereto.

As used in the present application, substantial sequence homology means close structural relationship between sequences of nucleotides or amino acids. For example, substantially homologous DNA sequences may be 60% homologous, preferably 80% and most preferably 90% or 95% homologous, or more, and substantially homologous amino acid sequences may preferably be 35%, more preferably 50%, most preferably more than 50% homologous. Homology also includes a relationship wherein one or several subsequences of nucleotides or amino acids are missing, or subsequences with additional nucleotides or amino acids are interdispersed.

The term "homology" as used herein not only embraces structural homology but also functional homology.

The invention thus further relates to a DNA sequence, which encodes a GA 20-oxidase obtainable from *Cucurbita maxima* or *Arabidopsis thaliana* or a protein having at least 35%, preferably at least 50%, and most preferably at least more than 50% homology therewith.

More specifically, the invention relates to a DNA having a sequence corresponding to the open reading frame of the sequence shown in SEQ ID NO 1, SEQ ID NO 3 and SEQ ID NO 5, or an equivalent sequence through the degeneracy of the genetic code, including derivatives capable of hybridizing with the sequence shown in SEQ ID NO 1, SEQ ID NO 3 or SEQ ID NO 5, and still encoding a polypeptide exhibiting GA 20-oxidase activity.

A preferred embodiment of the invention is therefore a substantially pure DNA as shown in SEQ ID NO 1, SEQ ID NO 3, or SEQ ID NO 5, or having substantial sequence homology to the sequence shown in SEQ ID NO 1, SEQ ID NO 3, or SEQ ID NO 5.

The DNA sequence according to the invention is preferably a recombinant DNA comprising a DNA sequence which encodes a recombinant polypeptide exhibiting GA 20-oxidase activity.

In one embodiment of the invention the recombinant DNA is in the form of a cDNA clone.

It is a further object of the invention to provide a chimeric gene construct comprising a DNA sequence encoding a polypeptide exhibiting GA 20-oxidase activity in operable linkage with plant expression signals including promoter and termination sequences capable of causing the gene to express a polypeptide exhibiting GA 20-oxidase activity within a plant, wherein the promoter sequences are preferably those of an inducible promoter or a tissue-preferential or a tissue-specific promoter.

The invention further comprises a chimaeric gene construct comprising at least a part of a reverse GA 20-oxidase nucleotide sequence, in operable linkage with plant expression signals including promoter and termination sequences capable of causing the reverse sequence to express antisense mRNA within a plant.

It is also an object of the invention to provide transformed host cells comprising recombinant DNA encoding a polypeptide exhibiting GA 20-oxidase activity in operable linkage with expression signals including promoter and termination sequences which permit expression of said DNA in the host cell.

A preferred embodiment of the invention is a transgenic plant including seed and progeny or propagules thereof comprising preferably stably integrated into its genome a chimeric gene construct as mentioned hereinbefore. Preferred is a monocotyledonous and a dicotyledonous plant, respectively such as tobacco, tomato, cotton, sunflower, maize, wheat and *Dactylis glomerata*.

Especially preferred is a transgenic plant which is a monocotyledonous plant, preferably a maize plant or a wheat plant.

The invention also comprises a recombinant polypeptide obtainable from plants or fungi exhibiting GA 20-oxidase activity, which polypeptide is preferably capable of acting essentially on one or more of the following substrates: $GA_{12}$, $GA_{53}$, $GA_{15}$ (open or closed lactone), $GA_{44}$ (open or closed lactone), $GA_{24}$, $GA_{19}$ and $GA_{23}$.

A preferred embodiment of the invention is therefore a recombinant polypeptide which exhibits a GA 20-oxidase activity and which is obtainable from plants or fungi, preferably from monocotyledonous and dicotyledonous plants, respectively, more preferably from dicotyledonous plants and most preferably from plants of the family Cucurbitaceae and Cruciferae respectively, such as *C. maxima* and *Arabidopsis thaliana*, or a protein having substantial homology thereto.

More specifically, the invention relates to a recombinant polypeptide having a sequence as shown in SEQ ID NO 2, SEQ ID NO 4 AND SEQ ID NO 6, or an sequence that is substantially homolgous thereto.

The invention further comprises a method of preparing a DNA sequence encoding a GA 20-oxidase, comprising preparing a cDNA library from a suitable source organism, and screening this library by means of one of the conventionally applied screening systems.

The invention also comprises a method of preparing a recombinant polypeptide exhibiting GA 20-oxidase activity, which comprises of one of the DNA sequences mentioned hereinbefore.

A further embodiment of the invention is a method of identifying DNA sequences comprising a DNA region encoding a polypeptide exhibiting GA 20-oxidase activity which method comprises preparing a cDNA or a genomic library from a suitable source organism and screening this library by means of hybridisation using a suitable DNA as a hybridisation probe.

In the first place, the present invention relates to a DNA sequence encoding a polypeptide exhibiting GA 20-oxidase activity.

Examples of a DNA sequence according to the invention are the open reading frames of the sequences shown in SEQ ID NO 1, SEQ ID NO 3 and SEQ ID NO 5 or an equivalent sequence through the degeneracy of the genetic code. Thus, a DNA sequence according to the invention may be one which codes for the amino acid sequence shown in SEQ ID NO 2, SEQ ID NO 4 and SEQ ID NO 6. It will be well understood that the invention includes derivatives and mutants of the sequences shown in SEQ ID NO 1, SEQ ID NO 3 and SEQ ID NO 5, provided that such derivatives encode essentially similar peptides having essentially the same function as the peptides encoded by the GA 20-oxidase gene described herein. The said derivatives of the DNA sequence according to the invention may be naturally occurring variants or mutants or, especially, they may be artificially created variants or mutants that may be produced specifically or unspecifically by known mutation methods.

Mutation is to be understood as meaning both the deletion or insertion of one or more bases and the substitution of one or more bases, or a combination of these measures. This is the case especially when the said base substitution is accompanied by a silent mutation which does not result in amino acid substitution and thus does not change the chemical structure of the expression product.

The structural gene according to the invention encoding GA 20-oxidase may constitute an uninterrupted coding sequence or it may include one or more introns, bounded by the appropriate splice junctions functional in plants, which may be obtained from a synthetic or a natural source. The structural gene according to the invention encoding GA 20-oxidase may further be obtained exclusively from naturally occurring or from synthetic sources. It may be obtained, for example, from a genomic or from a cDNA library or constructed entirely by synthetic means.

Another possibility is the construction of a hybrid DNA sequence comprising cDNA and also genomic DNA and/or synthetic DNA. In that case, the cDNA may originate from the same gene as the genomic DNA, or both the cDNA and the genomic DNA may originate from different gene sources. In any case, however, the genomic DNA and/or the cDNA may each be produced individually from the same gene or from different genes.

If the structural gene contains portions of more than one gene, these genes may originate from one and the same organism, from several organisms belonging to different strains or varieties of the same species or different species of the same genus, or from organisms belonging to more than one genus of the same or a different taxonomic unit.

In any event, the DNA sequence is considered to be within the scope of the invention, if the protein encoded has a GA 20-oxidase activity.

The invention also provides a method of preparing a recombinant DNA encoding GA 20-oxidase. The method may include preparing a cDNA library from a suitable source, and screening this library by means of an antibody against GA 20-oxidase or part of its amino acid sequence, or screening the library by testing for catalytic activity characteristic of the GA 20-oxidase or by any other suitable method known in the art. Standard techniques in recombinant DNA technology can be used as part of the method, such as hybridisation using cDNA probes, polymerase chain reaction using degenerate primers, and restriction fragment length polymorphism.

The method of preparing a recombinant DNA encoding GA 20-oxidase may include preparing a genomic or a cDNA gene library that can be produced by customary routine methods very well known to the person skilled in that field. The basic methods of producing genomic or cDNA gene libraries are described in detail, for example, in Maniatis et al (1982), while information relating to the transfer and application of those methods to plant systems will be found, for example, in the Mohnen (1985) reference [Mohnen et al, EMBO J., 4: 1631–1635 (1985)].

Genomic DNA and cDNA can be obtained in various ways. Genomic DNA, for example, can, using known methods, be extracted from suitable cells and purified.

In a specific embodiment of the present invention, the starting material used for the production of cDNA is generally mRNA, which can be isolated from selected cells or tissues, but especially from cells or tissues of immature seeds of Cucurbitaceae plants such as, for example, *C. maxima*, which are known to be a rich source of GA biosynthetic enzymes. A further suitable source of GA biosynthetic enzymes is the shoot tissue of *Arabidopsis thaliana* plants. The isolated mRNA can then be used in a reverse transcription as the matrix for the production of a corresponding cDNA.

The methods of isolating poly(A$^+$) RNA and of producing cDNA are known to the person skilled in the art and are described in detail below in the Examples.

The extracted and purified DNA preparations are then cleaved into fragments for the subsequent cloning. The genomic DNA or cDNA to be cloned may be fragmented to a size suitable for insertion into a cloning vector either by mechanical shearing or, preferably, by cleavage with suitable restriction enzymes. Suitable cloning vectors which are already being used as a matter of routine for the production of genomic and/or cDNA gene libraries include, for example, phage vectors, such as the λ Charon phages, or bacterial vectors, such as the *E. coli* plasmid pBR322. Further suitable cloning vectors are known to the person skilled in the art and may be obtained from commercial sources such as, for example, that contained in the 'Fast Track' mRNA isolation kit obtainable from INVITROGEN or the λgt11 Cloning Kit of Amersham.

From the gene libraries produced in that manner, suitable clones comprising the desired gene or parts thereof can then be identified in a screening program, for example with the aid of suitable oligonucleotide probes (probe molecule), and then isolated. Various methods are available for identifying suitable clones, for example differential colony hybridisation or plaque hybridisation. Immunological detection methods based on identification of the specific translation products may also be used.

There may be used as probe molecule, for example, a DNA fragment that has already been isolated beforehand from the same gene or from a structurally related gene and that is capable of hybridisation with the corresponding section of sequence within the desired gene that is to be identified.

Provided that the amino acid sequence of the gene to be isolated or at least parts of that sequence are known, a corresponding DNA sequence can be drawn up on the basis of that sequence information. On the basis of that information it is thus possible to draw up oligonucleotide molecules that can be used as probe molecules for the identification and isolation of suitable clones by hybridising the said probe molecules with genomic DNA or cDNA in one of the methods described above.

In order to facilitate detection of the desired gene, the above-described DNA probe molecule can be labelled with a suitable readily detectable group. Within the scope of this invention, a detectable group is to be understood as being any material having a particular readily identifiable physical or chemical property.

Such materials are already widely used especially in the field of immunoassays, and the majority of them may also be employed in the present Application. Special mention may be made at this point of enzymatically active groups, for example enzymes, enzyme substrates, coenzymes and enzyme inhibitors, and also of fluorescent and luminescent agents, chromophores and radioisotopes, for example, $^3$H, $^{35}$S, $^{32}$P, $^{125}$I and $^{14}$C. The ready detectability of these labels is based on the one hand on their inherent physical properties (e.g. fluorescent labels, chromophores, radioisotopes) and on the other hand on their reaction and binding properties (e.g. enzymes, substrates, coenzymes, inhibitors).

Also suitable as a probe molecule is a single-stranded cDNA derived from a poly(A)$^+$ RNA, which in turn is isolated from a tissue or a cell known to contain high levels of GA biosynthetic enzymes.

For example, the cDNA sequence of the present invention may be used to isolate genomic or further cDNA sequences encoding GA 20-oxidase. Where a partial cDNA has been obtained, the partial cDNA may be used as a probe to screen the cDNA library in order to isolate a full length cDNA clone. Hybridizing clones are purified, restriction mapped and sequenced. A full length clone will be near message size as well as having a complete open reading frame. To isolate a genomic clone, the full length cDNA is used as a probe to screen a genomic library. By restriction mapping and hybridization to the cDNA, the coding region of the genomic clone is identified. The area upstream from the coding area of the clone is the promoter region.

General methods relating to hybridisation are described, for example, in Maniatis T. et al (1982) and in Haymes B. T. et al (1985) [Haymes B. T. et al, Nucleic Acid Hybridisation: a Practical Approach, IRL Press, Oxford, England (1985)].

Those clones within the above-described gene libraries which are capable of hybridisation with a probe molecule and which can be identified by means of one of the above-mentioned detection methods can then be analysed further in order to determine in detail the extent and nature of the coding sequence.

An alternative method of cloning genes is based on the construction of a gene library composed of expression vectors. In that method, analogously to the methods already described above, genomic DNA, but preferably cDNA, is first isolated from a cell or a tissue capable of expressing a desired gene product—in the present case GA 20-oxidase—and is then spliced into a suitable expression vector. The gene libraries so produced can then be screened using suitable measures, preferably using antibodies, and those clones selected which comprise the desired gene or at least part of that gene as an insert.

Alternatively, total DNA from the DNA library, preferably from the cDNA library, can be prepared and used as a template for a PCR reaction with primers representing low degeneracy portions of the amino acid sequence. Preferably, the primers used will generate PCR products that represent a significant portion of the nucleotide sequence. The PCR products can be further probed to determine if they correspond to a portion of the GA 20-oxidase gene using a synthetic oligonucleotide probe corresponding to an amino acid fragment sequence located in the interior or middle region of the GA 20-oxidase protein.

The cDNA clones and PCR products prepared as described above or fragments thereof may be used as a hybridization probe in a process of identifying further DNA sequences from a homologous or a heterologous source organism encoding a protein product that exhibits GA 20-oxidase activity such as, for example, a fungi or a monocotyledonous plant. A suitable source would be developing tissue from maize or wheat plants.

They may also be used as a RFLP marker to determine, for example, the location of the GA-20 oxidase gene or a closely linked trait in the plant genome or for marker assisted breeding [EP-A 306,139; WO 89/07647].

Using the methods described above it is thus possible to isolate a gene that codes for a GA 20-oxidase.

For further characterisation, the DNA sequences purified and isolated as described above are subjected to sequence analysis. The previously isolated DNA is first cleaved into fragments by means of suitable restriction enzymes and then cloned into suitable cloning vectors, for example the M13 vectors mp 18 and mp 19. The sequencing is carried out in the 5' to 3' direction, the dideoxynucleotide chain termination method according to Sanger [Sanger et al, 1977] or the method according to Maxam and Gilbert [Maxam and Gilbert, 1980] or a commercially available nucleotide sequencing instrumentation [available from Applied Biosystems, Foster City, Calif. and Dupont, Wilmington, Del.] preferably being used. In order to avoid errors in sequencing, it is advantageous to sequence the two DNA strains in parallel. The analysis of the nucleotide sequence and of the corresponding amino acid sequence is advantageously computer-assisted using suitable commercially available computer software [e.g. GCG software of the University of Wisconsin].

The area upstream from the coding area of the clone is the promoter region. The GA 20-oxidase promoter region may be more precisely mapped through deletion analysis. 5' deletions of a GA 20-oxidase promoter are made by introducing restriction sites by PCR using oligonucleotide primers with restriction sites at the 5' ends and promoter sequences at the 3' ends. The PCR products are digested, purified, and cloned into a suitable cloning vector such as, for example, into pBI101 (Clontech). The deletion mutants contain the 5' untranslated leader sequence fused to the translational start site of the GUS gene. Internal and 3' deletions of the GA 20-oxidase promoter are made by PCR in a similar manner. The PCR fragments are fused to a GUS vector containing the CAMV 35S minimal promoter [−46 to +1; Benfey et al, 1990]. Transgenic plants are tested with the GUS fluorometric and histochemical assay.

The GA 20-oxidase promoter region may be suitably used within the scope of the present invention for the preparation of recombinant, or chimaeric, DNA constructs comprising a GA 20-oxidase structural gene, which may be of homologous or of heterologous origin relative to the promoter sequence.

The present invention thus further comprises recombinant DNA sequences comprising, in a 5' to 3' direction, a promoter region obtainable from a GA 20-oxidase genomic DNA sequence, which is operatively linked to a GA 20-oxidase coding DNA sequence, which may be homologous or heterologous relative to the promoter sequence. The recombinant DNA sequences result in expression of the associated homologous or heterologous GA 20-oxidase in transformed plant material.

In principle, the DNA can also be prepared by chemical synthesis.

In another aspect, the invention provides a recombinant polypeptide exhibiting GA 20-oxidase activity. This polypeptide or enzyme is soluble and 2-oxoglutarate-dependent. It is capable of acting on, for example, one or more of the following substrates: $GA_{12}$, $GA_{53}$, $GA_{15}$ (open or closed lactone), $GA_{44}$ (open or closed lactone), $GA_{24}$, $GA_{19}$ and $GA_{23}$. The GA 20-oxidase may be derived from plants or fungi, preferably from mono-cotyledonous and dicotyledonous plants respectively, and more preferably from dicotyledonous plants. A particularly suitable source is plants of the family Cucurbitaceae, such as C. maxima, of which the immature seeds are a convenient source. A further suitable source is plants of the family Cruciferae, such as Arabidopsis thaliana, of which shoot material is a convenient source.

In particular, the recombinant GA 20-oxidase is derived from C. maxima or Arabidopsis thaliana respectively, or is a protein having substantial homology thereto (as defined above).

An embodiment of this latter aspect of the invention is a GA 20-oxidase having the amino acid sequence shown in SEQ ID NO 2, SEQ ID NO 4 and SEQ ID NO 6. The invention also includes a protein having substantial homology (as defined above) with this amino acid sequence and having GA 20-oxidase activity. Modified proteins derived from this amino acid sequence by mutation, i.e. addition, substitution or deletion of one or more amino acid residues, and having GA 20-oxidase activity, are also included within the scope of the invention.

Once having identified and isolated the DNA encoding a polypeptide product exhibiting GA 20-oxidase activity, a purified protein can be obtained from transgenic expression of the said DNA, i.e., placing a recombinant DNA comprising a DNA sequence coding for a protein exhibiting GA 20-oxidase activity into an appropriate bacterial, yeast, plant or other suitable cell expression system.

Suitable hosts include bacteria such as E. coli and yeast, including the strain Saccharomyces cerevisiae. Other suitable expression system hosts include insect cells grown in culture. These insect cells may be infected with a baculovirus containing a recombinant DNA molecule according to the invention.

Alternatively, the baculovirus may be used to infect the cells of a living insect, and the insect cells used as the expression system host. The expression system host is then allowed to produce an expression supernatant. This allows facile generation of large amounts of purified recombinant GA 20-oxidase by isolating the enzyme from the expression supernatant.

A further object of the present invention is chimaeric gene constructions comprising, in addition to the DNA sequence according to the invention encoding GA 20-oxidase, expression signals which include both promoter and terminator sequences and other regulatory sequences of the 3' and 5' untranslated regions and which are operably linked to the coding DNA sequence such as to ensure the expression of the corresponding gene product in the respective host organism.

Suitable control sequences that are preferred within the scope of the invention are those comprising promoter and 5' and 3' untranslated regulatory sequences that are functional in plants. These sequences may, independently, be derived from any source, such as, for example, virus, plant or bacterial genes. These promoters or regulatory sequences can be constitutive in nature or can be regulated in their patterns of expression. Such regulation may be temporal or spatial and include developmentally regulated promoters and inducible promoters. Proteins may be optionally expressed in the vacuole or extracellularly using methods well-known in the art (EP 462,065).

In general, any promoter and any terminator capable of bringing about an induction of the expression of a coding DNA sequence (structural gene) may be used as a constituent of the chimaeric gene sequence according to the invention. The said expression signals may promote continuous and stable expression of the gene. Especially suitable are expression signals originating from genes of plants or plant viruses. Examples of suitable promoters and terminators are those of the Cauliflower Mosaic Virus genes (CaMV) or homologous DNA sequences that still have the characteristics properties of the mentioned expression signals. Also suitable are bacterial expression signals, especially the expression signals of the nopaline synthase genes (nos) or the opine synthase genes (ocs) from the Ti-plasmids of *Agrobacterium tumefaciens*. Also to be mentioned here are, for example, ubiquitine promoters, actin promoters, histone promoters and tubulin promoters. Other suitable promoters are an amylase promoter (a-amylase promoter) and an ABA (abscisic acid) inducible promoter.

In a further embodiment of the invention a promoter region may be used that is obtainable from a GA 20-oxidase genomic DNA sequence as described hereinbefore.

Within the scope of this invention, preference is given to the 35S and 19S expression signals of the CaMV genome or their homologues which can be isolated from the said genome using molecular biological methods, as described, for example, in Maniatis et al (1982), and linked to the coding DNA sequence.

Further preferred are expression signals that comprise tissue-preferential or tissue-specific promoters. The term tissue-preferential promoter is used to indicate that a given expression signal will promote a higher level of transcription of an associated expressible DNA, or of expression of the product of the said DNA as indicated by any conventional RNA or protein assay, or that a given DNA sequence will demonstrate some differential effect; i.e., that the transcription of the associated DNA sequences or the expression of a gene product is greater in some tissue than in all other tissues of the plant. For example, the tissue-preferential promoter may direct higher expression of an associated gene product in leaves, stems, roots and/or pollen than in seed. One example of a tissue-preferential promoter, which may be suitably used within the scope of the present invention, is a pith-preferred promoter isolated from a maize TrpA gene.

The term tissue-specific promoter is used to indicate that a given regulatory DNA sequence will promote transcription of an associated expressible DNA sequence entirely in one or more tissues of a plant, or in one type of tissue, while essentially no transcription of that associated coding DNA sequence will occur in all other tissues or types of tissues of the plant. Numerous promoters whose expression are known to vary in a tissue specific manner are known in the art. One such example is the maize phosphoenol pyruvate carboxylase [PEPC], which is green tissue-specific [Hudspeth R. L. and Grula J. W., 1989]. Other green tissue-specific promoters include chlorophyll a/b binding protein promoters and RubisCo small subunit promoters. Further to be mentioned here are, for example, pollen-specific promoters such as those obtainable from a plant calcium-dependent phosphate kinase [CDPK] gene.

A developmentally regulated promoter can also be used. Of course, in the present invention, any promoter which is functional in the desired host plant can be used to direct the expression of an associated gene.

In general, the GA 20-oxidase structural gene may be linked to the promoter region in either a sense or an anti-sense orientation.

It is often advantageous to incorporate a leader sequence between the promoter sequence and the adjacent coding DNA sequence, the length of the leader sequence being so selected that the distance between the promoter and the DNA sequence according to the invention is the optimum distance for expression of the associated structural gene. Suitable leader sequences include leader sequences of various lengths isolated from the 35S CaMV gene (Pierce et al., 1987). The preferred leader sequences are those isolated from the 35S CaMV gene, having a length from about 50 to about 130 nucleotides. The identification of other leader sequences is known in the art. See Della-Cioppa et al, 1987; Schecman, 1985.

Further regulatory DNA sequences that may be used for the construction of chimaeric genes include, for example, sequences that are capable of regulating the transcription of an associated DNA sequence in plant tissues in the sense of induction or repression.

There are, for example, certain plant genes that are known to be induced by various internal and external factors, such as plant hormones, heat shock, chemicals, pathogens, oxygen deficiency, light, stress, etc.

Another class of genes that are suitable in plants comprises the light-regulated genes, especially the nuclear-coded gene of the small subunit of ribulose-1,5-biphosphate carboxylase (RUBISCO). Morelli et al (1985) have shown that the 5'-flanking sequence of a RUBISCO gene from the pea is capable of transferring light-inducibility to a reporter gene, provided the latter is linked in chimaeric form to that sequence. It has also been possible to extend this observation to other light-induced genes, for example the chlorophyll-a/b-binding protein.

A further group of regulatable DNA sequences comprises chemically regulatable sequences that are present, for example, in the PR (pathogenesis-related) protein genes of tobacco and are inducible by means of chemical regulators such as those described in EP-A-332,104.

In a specific embodiment of the invention a promoter of the Arabidopsis PR1a gene is being used.

The regulatable DNA sequences mentioned by way of example above may be of both natural and synthetic origin, or they may comprise a mixture of natural and synthetic DNA sequences.

The recombinant DNA sequences of the present invention may further comprise a signal sequence, which is operatively linked to the coding DNA sequence. The signal sequence is responsible for specialized transport of the associated peptide within the plant cell.

The signal sequence of the present invention may be any DNA sequence which is able to direct the transport of an associated polypeptide into one or more of the cellular compartments. The signal sequence is preferably a sequence which is translated into a signal peptide, which becomes separated from the peptide after transit of the peptide is complete. Signal sequences are useful for directing the polypeptide product of the coding DNA sequence to a desired location within the cell, such as to the mitochondria or to the endoplasmic reticulum, or to direct extracellular transport outside of the cell.

To be mentioned here are, for example, N-terminal signal peptides, which are involved in intracellular transport and which can be found at the N-terminal end of proteins transported via the endomembrane system. These signal sequences ensure that the said proteins first pass into the endoplasmic reticulum, where the signal peptide is split off proteolytically from the precursor protein as soon as it has fulfilled its function. By virtue of its specific function, this type of signal peptide sequence has been conserved to a high degree during evolution in all living cells, irrespective of whether they are bacteria, yeasts, fungi, animals or plants.

At the C-terminal end of vacuolar proteins, on the other side, sequences may be found that are involved in directing the expression of the associated coding part of the plant vacuole. Examples of these so-called 'vacuolar targeting' sequences are provided, for example, in EP-A 462,065.

Moreover, the DNA molecule may comprise further sections of sequence that code for peptide fragments which as a whole contribute towards improving the competence for admission into the vacuole, for example the propeptide fragment discovered by Matsuoka K. and Nakamura K. in the N-terminal extension of sporamine [Matsuoka K. and Nakamura K. (1991)].

Further signal sequences useful for the present invention are, for example, the signal sequence from the pathogenesis-related gene (PR-1) of tobacco, which is described in Cornellisen et al, 1986; the yeast mitochondrial presequence; Schmitz et al, 1989; the signal sequence from plant mitochondrial Rieske iron-sulfur protein, Huang et al, 1991; mitochondrial and chloroplast targeting peptides, von Heijne et al, 1989.

The present invention therefore also includes chimaeric genetic constructions that comprise, in operable linkage with a structural gene encoding GA 20-oxidase, further regulatory sections of DNA sequence permitting, for example, specifically controlled induction or repression of gene expression.

As a modification of the above aspect, the invention also provides a chimaeric gene construct comprising at least a part of a reverse GA 20-oxidase nucleotide sequence, having at its 5'-end a promoter capable of causing the reverse sequence to express antisense mRNA within a plant and, optionally, further regulatory DNA sequences such as those mentioned above.

The various sections of the chimaeric DNA sequences according to the invention may be linked to one another by methods known per se to form a complete coding DNA sequence. Suitable methods include, for example, the in vivo recombination of DNA sequences having homologous sections and the in vitro linking of restriction fragments.

In the above in vivo and/or in vitro processes for assembling the different sections of the said functional unit, cloning vectors may be involved such as, for example, plasmid or virus (bacteriophage) vectors having replication and control sequences originating from species that are compatible with specific host cells.

The cloning vector generally carries an origin of replication, especially an origin of replication that is capable of functioning in *E. coli*, in Agrobacterium or in both, and, in addition, specific genes that lead to phenotypic selection features in the transformed host cell, especially to resistance to antibiotics or to specific herbicides. The transformed vectors can be selected on the basis of those phenotypic markers after transformation in a host cell.

The cloning vectors and the host cell transformed with those vectors are generally used to increase the number of copies of the constructs cloned therein. With an increased number of copies it is possible to isolate the vector carrying the chimaeric gene construction and prepare it, for example, for insertion of the chimaeric gene sequence into a plant cell.

Especially suitable within the scope of the present invention are so called shuttle vectors, which can stably replicate not only in one but in at least two different host organisms such as, for example, in *E. coli* and in *Agrobacterium tumefaciens*, in the presence of a suitable selection marker.

Selectable phenotypic markers that may be used within the scope of this invention include, for example, resistance to ampicillin, tetracycline, hygromycin, kanamycin, methotrexate, G418 and neomycin, but this list, which is given by way of example, is not intended to limit the subject of the invention.

Suitable host cells within the scope of this invention are prokaryotes, including bacterial hosts, for example *A. tumefaciens, E. coli, S. typhimurium* and *Serratia marcescens*, and also cyanobacteria. Eukaryotic hosts, such as yeasts, mycelium-forming fungi and plant cells, may also be used within the scope of this invention.

The splicing of the chimaeric gene construction according to the invention into a suitable cloning vector is carried out using standard methods, such as those described, for example, in Maniatis et al (1982) and Sambrook et al (1989).

In a further process step, the cloned structural gene coding for GA 20-oxidase may be introduced into one of the commonly used plant transformation cassettes and transformed into a plant cell using standard techniques and, optionally, integrated into the plant genome.

The detection of transformed plant cell may be accomplished using suitable selection systems.

Very convenient selection systems that are preferably applied in transient expression systems are those that are based on a scorable marker such as, for example, regulatory or structural genes controlling anthocyanin biosynthesis, GUS (β-glucuronidase), luciferase, opine synthetases, thaumatin, β-galactosidase, unique synthetic epitopes designed for easy detection by ELISA, phycobiliproteins and various fluorogenic substances.

In a specific embodiment of the present invention use is made of the 'GUS'-based marker system, which involves a DNA sequence encoding a β-glucuronidase enzyme operably linked with one or more of the expression signals listed above. Upon expression of the GUS gene in the plant cell the β-glucuronidase enzyme may react with its specific substrate, which leads to the appearance of blue spots that can be easily detected in the plant tissue.

In a further embodiment of the present invention the use is made of coding sequences for the anthocyanin regulatory genes known in the art as C1 and B-Peru [Goff et al, 1990]. Such coding sequences, operably linked to one or more of the several constitutive promoters listed above, can be used to isolate transformants on the basis of the red pigmentation of cells transformed with such genes. The 'anthocyanin'-based marker system, on the other hand, involves a red colour reaction.

In a further aspect, the invention provides a transformed host cell comprising recombinant DNA encoding a polypeptide exhibiting GA 20-oxidase activity in operable linkage with expression signals including promoter and termination sequences which permit expression of said DNA in the host cell. Where the host cell is a plant cell, transgenic plants can be obtained. Thus, the invention provides for the first time a transgenic plant with an altered GA biosynthetic pathway, in particular one which contains and is capable of expressing a recombinant GA:2-oxoglutarate dioxygenase gene. Thus, there is provided a transgenic plant comprising a recombinant DNA encoding a polypeptide exhibiting GA 20-oxidase activity in operable linkage with plant expression signals including promoter and termination sequences which permit expression of said DNA in the plant.

A modification of the above aspect of the invention is the transformation of a plant with a construct containing a reverse GA 20-oxidase nucleotide sequence (the entire coding sequence or a part thereof) for transcription of antisense mRNA and consequent reduced expression of the GA 20oxidase gene. Examples of antisense technology are provided in EP-A 240 208 (Calgene) and EP-A 458 367 (Calgene). The reverse nucleotide sequence may be in association with a promoter which is specific to certain plant tissues and/or to external stimulus (e.g. light, cold, heat, chemicals etc.). Another possible means of reducing expression is for example the use of ribozyme technology as described in EP-A 321 201 or WO 89/05852. A combination of antisense and ribozyme technology may also be used within the scope of the present invention for regulating GA 20-oxidase activity.

Also an overexpression of the GA 20-oxidase gene in plants may result in reduced levels of biologically active gibberellins in plants.

The invention includes progeny or propagules, including seed, of transgenic plants as defined above. The invention also includes methods of making such transgenic plants.

The recombinant DNA according to the invention comprising the GA 20-oxidase encoding DNA sequence can be introduced into the plant cell in a number of ways that are well known to those of skill in the art. For example, methods of transforming plant cells include microinjection [Crossway et al (1986); Neuhaus (1987)], electroporation [Riggs et al (1986)], Agrobacterium mediated transformation [Hinchee et al (1988)], direct gene transfer [Paszkowski et al, (1984)], and ballistic particle acceleration using, for example, devices available from Agracetus, Inc., Madison, Wis. and Dupont, Inc., Wilmington, Del. [see, for example, Sanford et al, U.S. Pat. No. 4,945,050, and McCabe et al, (1988). Also see, Weissinger et al (1988); Sanford et al (1987) (onion); Christou et al (1988) (soybean); McCabe et al (1988) (soybean); Datta et al (1990) (rice); Klein et al (1988) (maize); Klein et al (1988) (maize); Klein et al (1989) (maize); Fromm et al (1990); Gordon-Kamm et al (1990) (maize)].

One possible method for introducing genetic material into plant cells comprises, for example, bringing plant cells into contact with viruses or with Agrobacterium comprising the DNA to be introduced. This may be achieved by infecting sensitive plant cells or by co-cultivating protoplasts derived from plant cells. Within the scope of this invention, Cauliflower Mosaic Virus (CaMV) may be used as a vector for the insertion of the GA 20-oxidase-encoding DNA sequence according to the invention into a plant.

Another method of inserting GA 20-oxidase-encoding DNA sequence into a cell makes use of the infection of the plant cell with *Agrobacterium tumefaciens* and/or *Agrobacterium rhizogenes,* which has previously been transformed with the said gene construction. The transgenic plant cells are then cultured under suitable culture conditions known to the person skilled in the art, so that they form shoots and roots and whole plants are finally formed.

A further possible method of transforming plant material comprises mixed infection using both *Agrobacterium rhizogenes* and transformed *Agrobacterium tumefaciens,* as described by Petit et al (1986) for the transformation of carrots.

The GA 20-oxidase-encoding DNA sequence according to the invention can therefore be transferred into suitable plant cells by means of, for example, the Ti-plasmid of *Agrobacterium tumefaciens* or the Ri-plasmid of *Agrobacterium rhizogenes.* The Ti-plasmid or Ri-plasmid is transferred to the plant in the course of infection by Agrobacterium and integrated in stable manner into the plant genome.

Any T-DNA-containing vector that can be transferred into plant cells and permits selection of the transformed cells is suitable for use within the scope of this invention such as, for example, a shuttle vector that comprises the GA 20-oxidase-encoding DNA sequence according to the invention cloned in between the left border sequence (LB) and the right border sequence (RB) and that is capable of stable replication both in *E. coli* and in *A. tumefaciens.* Preferred is a so-called binary vector system.

Using newly developed transformation techniques, it has also become possible in principle to transform in vitro plant species that are not natural host plants for Agrobacterium. For example, monocotyledonous plants, especially the cereal species and various grasses, are not natural hosts for Agrobacterium.

It has become increasingly evident that monocotyledons can also be transformed using Agrobacterium, so that, using new experimental formulations that are now becoming available, cereals and grass species are also amenable to transformation [Grimsley N. H. et al (1987)].

One of the preferred methods for introducing DNA into a plant cell by means of Agrobacterium is the so-called leaf disk transformation using Agrobacterium [Horsch et al (1985)]. Sterile leaf disks from a suitable target plant are incubated with Agrobacterium cells comprising one of the GA 20oxidase-encoding DNA sequence according to the invention, and are then transferred into or onto a suitable nutrient medium. Especially suitable, and therefore preferred within the scope of this invention, are LS media that have been solidified by the addition of agar and enriched with one or more of the plant growth regulators customarily used, especially those selected from the group of the auxins consisting of a-naphthylacetic acid, picloram, 2,4,5-trichlorophenoxyacetic acid, 2,4-ichlorophenoxyacetic acid, indole-3-butyric acid, indole-3-lactic acid, indole-3-succinic acid, indole-3-acetic acid and p-chlorophenoxyacetic acid, and from the group of the cytokinins consisting of kinetin, 6-benzyladenine, 2-isopentenyladenine and zeatin. The preferred concentration of auxins and cytokinins is in the range of from 0.1 mg/l to 10 mg/l.

After incubation for several days but preferably after incubation for 2 to 3 days at a temperature of from 20 C. to 40 C., preferably from 23 C. to 35 C. and more especially at 25 C. and in diffuse light, the leaf disks are transferred to a suitable medium for the purpose of shoot induction. Especially preferred for the selection of the transformants is an LS medium that does not contain auxin but contains cytokinin instead, and to which a selective substance has been added dependent on the marker gene used. The cultures are kept in the light and are transferred to fresh medium at suitable intervals, but preferably at intervals of one week. Developing green shoots are cut out and cultured further in a medium that induces the shoots to form roots. Especially preferred within the scope of this invention is an LS medium that does not contain auxin or cytokinin but to which a selective substance has been added for the selection of the transformants.

In addition to Agrobacterium-mediated transformation, within the scope of this invention it is possible to use direct transformation methods for the insertion of the gene constructions according to the invention into plant material.

Possible methods for the direct transfer of genetic material into a plant cell comprise, for example, the treatment of protoplasts using procedures that modify the plasma membrane, for example, polyethylene glycol treatment, heat shock treatment or electroporation, or a combination of those procedures [Shillito et al (1985)].

In the electroporation technique, plant protoplasts together with plasmids that comprise the GA 20oxidase-encoding DNA sequence are subjected to electrical pulses of high field strength. This results in a reversible increase in the permeability of biomembranes and thus allows the insertion of the plasmids. Electroporated plant protoplasts renew their cell wall, divide and form callus tissue. Selection of the transformed plant cells can take place with the aid of the above-described phenotypic markers.

A further method for the direct introduction of genetic material into plant cells, which is based on purely chemical procedures and which enables the transformation to be carried out very efficiently and rapidly, is described in Negrutiu I. et al (1987).

Also suitable for the transformation of plant material is direct gene transfer using co-transformation (Schocher R. J. et al 1986).

Co-transformation is a method that is based on the simultaneous taking up and integration of various DNA molecules (non-selectable and selectable genes) into the plant genome and that therefore allows the detection of cells that have been transformed with non-selectable genes.

Further means for inserting genetic material contained in a vector directly into a plant cell comprise using purely physical procedures, for example by microinjection using finely drawn micropipettes [Neuhaus et al (1987)] or by bombarding the cells with microprojectiles that are coated with the transforming DNA ["Microprojectile Bombardment"; Wang Y-C et al (1988)] or are accelerated through a DNA containing solution in the direction of the cells to be transformed by a pressure impact thereby being finely atomized into a fog with the solution as a result of the pressure impact [EP-A434,616].

Microprojectile bombardment has been advanced as an effective transformation technique for cells, including cells of plants. In Sanford et al (1987) it was reported that microprojectile bombardment was effective to deliver nucleic acid into the cytoplasm of plant cells of *Allium cepa* (onion). Christou et al (1988) reported the stable transformation of soybean callus with a kanamycin resistance gene via microprojectile bombardment. Christou et al reported penetration at approximately 0.1% to 5% of cells. Christou further reported observable levels of NPTII enzyme activity and resistance in the transformed calli of up to 400 mg/l of kanamycin. McCabe et al (1988) report the stable transformation of *Glycine max* (soybean) using microprojectile bombardment. McCabe et al further report the recovery of a transformed $R_1$ plant from an $R_0$ chimaeric plant.

The transformation of maize plants, including elite maize plants, by microprojectile bombardment can be carried out according to the general protocol described for example in EP-A 478 502, the disclosure of which is incorporated herein by reference.

The list of possible transformation methods given above by way of example is not claimed to be complete and is not intended to limit the subject of the invention in any way.

The present invention therefore also comprises transgenic plant material, selected from the group consisting of protoplasts, cells, calli, tissues, organs, seeds, embryos, ovules, zygotes, etc. and especially, whole and preferably phenotypically normal plants, that has been transformed by means of the processes described above and comprises the recombinant DNA according to the invention in expressible form, and processes for the production of the said transgenic plant material.

Preferred within the present invention are monocotyledonous plants including seed and the progeny or propagueles thereof, but especially graminaceous monocots such as, for example, Lolium, Zea, Triticum, Triticale, Sorghum, Saccharum, Bromus, Oryzae, Avena, Hordeum, Secale and Setaria. Especially preferred are transgenic maize, wheat, and barley plants and seed thereof. Most preferred is the *Zea mays* Elite inbred line Funk 2717.

Screening of plant cells, tissue and plants for the presence of specific DNA sequences may be performed by Southern analysis (Southern, 1975). Details of this procedure are given in Maniatis et al (1982). This screening may also be performed by the use of Polymerase Chain Reaction procedures (PCR). PCR procedures are described in detail in Mullis et al (1987) and EhrlichA(1989).

Transformation of the plant cells includes separating transformed cells from those that have not been transformed. One convenient method for such separation or selection is to incorporate into the material to be inserted into the transformed cell a gene for a selection marker. As a result only those cells that have been successfully transformed will contain the marker gene. The translation product of the marker gene will then confer a phenotypic trait that will make selection possible. Usually the phenotypic trait is the ability to survive in the presence of some chemical agent, such as an antibiotic, e.g., kanamycin, G418, paromomycin, etc., which is placed in a selection media.

Some examples of genes that confer antibiotic resistance include, for example, those coding for neomycin phosphotransferase kanamycin resistance, [Velten et al (1984)]; hygromycin phosphotransferase (hygromycin resistance, [van den Elzen et al (1985)], the kanamycin resistance (NP II) gene derived from Tn5 Bevan et al (1983); [McBride et al (1990)], the PAT gene described in Thompson et al (1987), and chloramphenicol acetyl-transferase.

An example of a gene useful primarily as a screenable marker in tissue culture for identification of plant cells containing genetically engineered vectors is a gene that encodes an enzyme producing a chromogenic product. One example is the gene coding for production of β-glucuronidase (GUS). This enzyme is widely used and its preparation and use is described in Jefferson (1987).

Once the transformed plant cells have been cultured on the selection media, surviving cells are selected for further study and manipulation. Selection methods and materials are well known to those of skill in the art, allowing one to choose surviving cells with a high degree of predictability that the chosen cells will have been successfully transformed with exogenous DNA.

After transformation of the plant cell or plant using, for example, the Agrobacterium Ti-plasmid, those plant cells or plants transformed by the Ti-plasmid so that the enzyme is expressed, can be selected by an appropriate phenotypic marker. These phenotypical markers include, but are not limited to, antibiotic resistance. Other phenotypic markers are known in the art and may be used in this invention.

Positive clones are regenerated following procedures well-known in the art. Subsequently transformed plants are evaluated for the presence of the desired properties and/or the extent to which the desired properties are expressed. A first evaluation may include, for example, the level of bacterial/fungal resistance of the transformed plants, stable heritability of the desired properties, field trials and the like.

The process for the production of transformed plant material, including whole plants, thus essentially comprises:
first isolating from a suitable source or synthesising by means of known processes a DNA sequence encoding a protein exhibiting GA 20-oxidase activity;
operably linking the said DNA sequence in a 5' to 3' direction to plant expression sequences as defined hereinbefore;

transforming the construct of step (b) into plant material by means of known processes and expressing it therein;

screening of the plant material treated according to step (c) for the presence of a DNA sequence encoding a protein exhibiting GA 20-oxidase activity; and optionally regenerating the plant material transformed according to step (c) to a whole and preferably phenotypically normal plant.

The present invention thus also comprises transgenic plants and the sexual and/or asexual progeny thereof, which have been transformed with a recombinant DNA sequence according to the invention.

The expression "asexual or sexual progeny of transgenic plants" includes by definition according to the invention all mutants and variants obtainable by means of known processes, such as for example cell fusion or mutant selection and which still exhibit the characteristic properties of the initial transformed plant, together with all crossing and fusion products of the transformed plant material.

Another object of the invention concerns the proliferation material of transgenic plants. The proliferation material of transgenic plants is defined relative to the invention as any plant material that may be propagated sexually in vivo or in vitro. Particularly preferred within the scope of the present invention are protoplasts, cells, calli, tissues, organs, seeds, embryos, egg cells, zygotes, together with any other propagating material obtained from transgenic plants.

A further aspect of the invention is the provision of an antibody raised against at least a part of the amino acid sequence of GA 20-oxidase. Such antibody is useful in screening a cDNA library in suitable vectors derived from plant tissue RNA.

The GA 20-oxidase gene according to the invention is useful in the modification of growth and developmental processes in transgenic plants. For example, reduced expression with antisense RNA may result in low GA production and therefore decreased elongation growth. The 20-oxidase is a regulatory enzyme and GA production may be particularly sensitive to its activity. It is known to be regulated by day length in long-day rosette plants, such as spinach, in which increased 20-oxidase activity in long days is responsible for bolting. Modifying the expression of this gene may therefore be of particular benefit. Other GA-regulated processes that are potential targets for manipulation are seed germination, flower initiation and development, fruit set and growth and sex expression in some dioecious species.

Thus, in one aspect of the use of this invention, reverse 20-oxidase nucleotide sequences and tissue and/or stimulus (e.g. light, heat, cold, chemical etc.)—specific promoters are used for transformation of plants so as to transcribe antisense mRNA, resulting in reduced expression of the 20-oxidase gene. This method produces plants with reduced endogenous GA levels and consequently altered growth habit and/or other developmental processes.

This method can be used to reduce vegetative growth as in:
straw strengthening in small grain cereals and rice;
for the prevention of lodging;
preventing lodging in oilseed rape and improving its canopy structure;
improving seedling quality for transplantation;
reducing growth of turf and amenity grasses;
reducing shoot growth in orchard and amenity trees; producing ornamental plants with more compact growth habits;
improving tolerance to cold, drought and fungal infection; and
increasing yields by diversion of assimilates from vegetative to reproductive organs.

The method is also useful to prevent bolting and flowering in rosette plants, e.g. sugar beet, lettuce, spinach and brassicas. It is useful to prevent sprouting, as in potato tubers. It is also useful to prevent precocious seed germination.

The invention is also useful in the transformation of plants with constructs containing the 20-oxidase sequence and tissue and/or stimulus-specific promoters for increased expression of the GA 20-oxidase gene. This method will increase the levels of biologically active GAs and so modify plant development, in cases where 20-oxidation is a rate-limiting step. The method can be used to improve fruit-set and growth as in: increasing berry size in seedless grapes (also to increase rachis length and produce a less compact cluster); increasing fruit set in citrus, particularly in clementines; delaying ripening in citrus; improving fruit set in pear and to decrease seed number, and to modify shape of apple fruit and improve skin texture.

The method can potentially be used to increase stem extension and leaf expansion, for example to increase stem length and sugar yield in sugar cane; to increase yield and earliness in celery and rhubarb; to increase yield in cabbage, lettuce, spinach etc.; and to increase forage yields in grasslands. The method can be used to stimulate seed germination, for example in the advancement of malting and increase in malt yields in cereals (e.g. barley, wheat, oats). The method can be used to produce uniform bolting and to stimulate flowering, for example in seed production in lettuce and other rosette species, or in advanced cropping of artichokes. The method can be used to induce flower formation in conifers. It can also be used to overcome dormancy of tubers and to hasten shoot emergence as in potatoes, sweet yams etc. Furthermore, the method can be used to induce staminate flowers in gynoecious species, such as cucumber.

Reference is now made to the accompanying sequence listing and the drawings, in which:

SEQ ID NO 1 shows the nucleotide sequence of GA 20-oxidase cDNA clone pB11 obtained from *Curcubita maxima* seed.

SEQ ID NO 2 shows the amino acid sequence of the GA 20-oxidase protein corresponding to cDNA clone pB11.

SEQ ID NO 3 shows the nucleotide sequence of GA 20-oxidase cDNA clone pAt2301 obtained from *Arabidopsis thaliana*.

SEQ ID NO 4 shows the amino acid sequence of the GA 20-oxidase protein corresponding to cDNA clone pAT2301.

SEQ ID NO 5 shows the nucleotide sequence of GA 20-oxidase cDNA clone pAt2353 obtained from *Arabidopsis thaliana*.

SEQ ID NO 6 shows the amino acid sequence of the GA 20-oxidase protein corresponding to cDNA clone pAt2353.

SEQ ID NO 7 shows the amino acid sequence of a synthetic peptide that had been produced on the basis of the amino acid sequence of a peptide resulting from trypsin digestion of purified $GA_{12}$ 20-oxidase from *C. maxima* endosperm.

SEQ ID NOs 8 and 9 show the amino acid sequence of two peptides corresponding to oligodeoxynucleotide primers that are designed based on amino acid regions conserved between the *Cucurbita maxima* cotyledon gibberellin 20-oxidase and other plant dioxygenases, including the tomato E8 ripening-related protein, tomato ethylene-forming enzyme, hyoscamine 6-hydroxylase from *Hyoscyamus niger*, barley flavanone 3-hydroxylase and the A2 gene from maize.

SEQ ID NOs 10 and 11 show the sequence of two oligodeoxynucleotide primers that are designed based on amino acid regions conserved between the *Cucurbita maxima* cotyledon gibberellin 20-oxidase and other plant dioxygenases, including the tomato E8 opening-related protein, tomato ethylene-froming enzyme, hyoscamine 6-hydroxylase from *Hyoscyamus niger*, barley flavanone 3-hydroxylase and the A2 gene from maize. The upstream and downstream primers contained restriction endonuclease cleavage sites for HindIII and EcoRI, respectively, at their 5' termini.

SEQ ID NOs 12 and 13 show the nucleotide and the corresponding amino acid sequence of an insert of cDNA clone pAt2204, whose predicted amino acid sequence is 67% identical to that of pumpkin gibberellin 20-oxidase.

SEQ ID NOs 14 to 17 show the nucleotide sequences of four oligonucleotides, which are used in conjunction with the M13 universal sequencing primer in PCR reactions.

SEQ ID NOs: 18 and 19 show molecular adaptors.

The invention is further illustrated by the following Examples. In the Examples, the isolation and nucleotide sequence of a cDNA clone for $GA_{12}$ 20-oxidase selected with a specific antibody from a λgt11 library derived from immature *Cucurbita maxima* (pumpkin) cotyledons are described. The identity of the cloned gene is confirmed by expression in *Escherichia coli* of a functional recombinant protein, which catalyses the three-step oxidation of $GA_{12}$ to $GA_{25}$ and of $GA_{53}$ to $GA_{17}$, as well as the formation in low yields of $C_{19}$-GAs. Furthermore, 20-oxidase activity in individual bacteriophage plaques can be detected.

The demonstration of 20-oxidase activity in individual bacteriophage plaques suggests that, in the absence of a suitable antibody, a functional screen of the λgt11 library based on measurement of enzyme catalytic activity would be successful. It will be possible to follow enzyme activity through sub-divisions of the library and then to select individual lysogenic colonies or plaques. Indeed, a low level of 20-oxidase activity in lysogens prepared using $3.6 \times 10^7$ pfu from the amplified library can be detected.

The Examples further describe the preparation of chimeric DNA constructs comprising the GA 20-oxidase cNDA in sense and antisense orientation, which are suitable to be transformed and expressed in plants. The Examples also describe the transformation of plants with the said chimeric constructs selected from the group consisting of tobacco, carrot, sunflower, tomato, cotton, *Zea mays, Dactylis glomerata* and wheat Further, in the Examples, the isolation of three additional cDNA clones [pAT2301; pAT2353; pYAP169] for $GA_{12}$ 20-oxidase from a λgt11 library derived from shoot tissue of the *Arabidopsis thaliana* gal mutant are described. The nucleotide and amino acid sequences respectively of cDNA clones pAT2301 and pAT2353 are shown in SEQ ID NO 1 to 6.

The Examples further describe the preparation of chimeric DNA constructs comprising the GA 20-oxidase cNDAs [AT2301; AT2353; YAP169] in sense and antisense orientation, which are suitable to be transformed and expressed in *Arabidopsis thaliana* plants and also the transformation of *Arabidopsis thaliana* with the said chimeric constructs.

REFERENCE EXAMPLE

General Recombinant DNA Techniques

Since many of the recombinant DNA techniques employed in this invention are a matter of routine for the person skilled in the art, it is better to give a short description of these generally used techniques here rather than to describe them every time they occur. Except where there is a specific indication to the contrary, all these procedures are described in the Maniatis et al (1982) reference.

A. Cleaving with restriction endonucleases

A reaction batch typically contains about 50 to 500 mg/ml of DNA in the buffer solution recommended by the manufacturer, New England Biolabs, Beverly, Mass. 2 to 5 Units of endonucleases are added for each mg of DNA and the reaction batch is incubated for from one to three hours at the temperature recommended by the manufacturer. The reaction is terminated by heating at 65 C. for 10 minutes or by extraction with phenol, followed by precipitation of the DNA with ethanol. This technique is also described on pages 104 to 106 of the Maniatis et al (1982) reference.

B. Treatment of DNA with polymerase in order to produce blunt ends 50 to 500 mg/ml of DNA fragments are added to a reaction batch in the buffer recommended by the manufacturer, New England Biolabs. The reaction batch contains all four deoxynucleotide triphosphates in concentrations of 0.2 mM. The reaction takes place over a period of 30 minutes at 15 C. and is then terminated by heating at 65 C. for 10 minutes. For fragments obtained by cleaving with restriction endonucleases that produce 5'-projecting ends, such as EcoRI and BamHI, the large fragment, or Klenow fragment, of DNA polymerase is used. For fragments obtained by means of endonucleases that produce 3'-projecting ends, such as PstI and SacI, the T4 DNA polymerase is used. The use of these two enzymes is described on pages 113 to 121 of the Maniatis et al (1982) reference.

C. Agarose gel electrophoresis and purification of DNA fragments from gels

Agarose gel electrophoresis is carried out in a horizontal apparatus, as described on pages 150 to 163 of the Maniatis et al reference. The buffer used is the tris-borate buffer described therein. The DNA fragments are stained using 0.5 mg/ml of ethidium bromide which is either present in the gel of tank buffer during electrophoresis or is added after electrophoresis. The DNA is made visible by illumination with long-wave ultraviolet light. If the fragments are to be separated from the gel, an agarose is used that gels at low temperature and is obtainable from Sigma Chemical, St. Louis, Mi. After the electrophoresis, the desired fragment is cut out, placed in a plastics test tube, heated at 65 C. for about 15 minutes, extracted three times with phenol and precipitated twice with ethanol. This procedure is slightly different from that described by Maniatis et al (1982) on page 170.

As an alternative, the DNA can be isolated from the agarose with the aid of the Geneclean kit (Bio 101 Inc., La Jolla, Calif., USA).

D. Addition of synthetic linker fragments to DNA ends

If it is desired to add a new endonuclease cleavage site to the end of a DNA molecule, the molecule is optionally first treated with DNA-polymerase in order to produce blunt ends, as described in the section above. About 0.1 to 1.0 Amg of this fragment is added to about 10 ng of phosphorylated linker DNA, obtained from New England Biolabs, in a volume of 20 to 30 ml with 2ml of T4 DNA ligase from New England Biolabs, and 1 mM ATP in the buffer recommended by the manufacturer. After incubation overnight at 15 C., the reaction is terminated by heating at 65 C. for 10 minutes.

The reaction batch is diluted to about 100 ml in a buffer appropriate for the restriction endonuclease that cleaves the synthetic linker sequence. About 50 to 200 units of this endonuclease are added. The mixture is incubated for 2 to 6 hours at the appropriate temperature, then the fragment is subjected to agarose gel electrophoresis and purified as described above. The resulting fragment will then have ends with endings that were produced by cleaving with the restriction endonuclease. These are usually cohesive, so that the resulting fragment can then readily be linked to other fragments having the same cohesive ends.

E. Removal of 5'-terminal phosphates from DNA fragments

During the plasmid cloning steps, treatment of the plasmid with phosphatase reduces the recircularisation of the vector (discussed on page 13 of the Maniatis et al reference). After cleavage of the DNA with the correct restriction endonuclease, one unit of calf intestinal alkaline phosphatase obtained from Boehringer-Mannheim, Mannheim, is added. The DNA is incubated at 37 C. for one hour and then extracted twice with phenol and precipitated with ethanol.

F. Linking of DNA fragments

If fragments having complementary cohesive ends are to be linked to one another, about 100 ng of each fragment are incubated in a reaction mixture of 20 to 40 ml containing about 0.2 unit of T4 DNA ligase from New England Biolabs in the buffer recommended by the manufacturer. Incubation is carried out for 1 to 20 hours at 15 C. If DNA fragments having blunt ends are to be linked, they are incubated as above except that the amount of T4 DNA ligase is increased to 2 to 4 units.

G. Transformation of DNA into E. coli

E. coli strain HB101 is used for most of the experiments. DNA is introduced into E. coli using the calcium chloride method, as described by Maniatis et al (1982), pages 250 and 251.

H. Screening of E. coli for plasmids

After transformation, the resulting colonies of E. coli are tested for the presence of the desired plasmid by means of a rapid plasmid isolation process. Two customary processes are described on pages 366 to 369 of the Maniatis et al (1982) reference.

I. Large-scale isolation of plasmid DNA

Processes for the isolation of plasmids from E. coli on a large scale are described on pages 88 to 94 of the Maniatis et al (1982) reference.

J. Cloning in M13 phage vectors

In the following description it is to be understood that the double-stranded replicative form of the phage M13 derivatives is used for routine processes, such as cleaving with restriction endonuclease, linking etc.

Unless there is a specific indication to the contrary, enzymes can be obtained from Boehringer, Biolabs (BRL). They are used in accordance with the manufacturer's instructions unless otherwise indicated.

K. Southern blot analysis

The extracted DNA is first treated with restriction enzymes, then subjected to electrophoresis in a 0.8% to 1% agarose gel, transferred to a nitrocellulose membrane [Southern E. M. (1975)] and hybridised with the DNA to be detected which has previously been subjected to nick-translation (DNA-specific activities of $5\times10^8$ to $10\times10^8$ c.p.m/mg). The filters are washed three times for 1 hour each time with an aqueous solution of 0.03M sodium citrate and 0.3M sodium chloride at 65 C. The hybridised DNA is made visible by blackening an X-ray film over a period of 24 to 48 hours.

EXAMPLE 1

Metabolism of $[^{14}C]$GAs by C. maxima poly(A)$^+$ RNA in vitro translation products Endosperm and developing cotyledons of pumpkin (C. maxima) are rich sources of GA-biosynthetic enzymes. Poly(A)$^+$ RNA was isolated from immature cotyledons(1 g) or endosperm (10 g) of C. maxima seed at 50% maturity index using the 'Fast Track' mRNA isolation kit (Invitrogen). The yield of poly(A)$^+$ RNA from cotyledons (17.4 mg/g fresh weight) was much higher than that from endosperm (0.75 mg/g fresh weight).

In vitro translation of mRNA from cotyledons (1 mg), or endosperm (0.5 mg), was performed with rabbit reticulocyte lysates (Boehringer) using standard conditions, except that leucine and methionine were at 12.5 mM. As controls the reticulocyte lysate was incubated with tobacco mosaic virus RNA (1 mg), and cotyledon mRNA (1 mg) was incubated without lysate. After incubating for 2 h at 30° C. the mixtures (50 ml) were supplemented with dioxygenase co-factors (4 mM 2-oxoglutarate, 0.5 mM FeSO$_4$, 3 mM ascorbate and catalase (1 mg/ml)) and $[^{14}C]$ GA substrate (15,000 dpm; specific radio-activity 180 Ci/mol) added in 5 ml, and incubated for a further 3 h. Products were extracted and separated by reverse-phase high-performance liquid chromatography (HPLC) connected on-line to a radioactivity monitor.

The products after translation of poly(A)$^+$ RNA from both tissues in rabbit reticulocyte lysates were shown to convert $[^{14}C]$ GA$_{12}$ to $[^{14}C]$ GA$_{15}$ after incubation with the appropriate co-factors and analysis by HPLC. This 20-oxidase activity was higher in the translation products derived from the cotyledon mRNA. No activity was detected after incubation of the reticulocyte lysate with tobacco mosaic virus RNA or of the cotyledon mRNA without the translation system.

EXAMPLE 2

Metabolism of $[^{14}C]$ GAs by Recombinant Bacteriophage Plaques

An amplified cDNA library in λgt11 derived from cotyledon poly(A)$^+$ RNA was immuno-screened with an antibody raised against a synthetic peptide (ValPheGlyGlySerAspGluSerLys) that had been produced on the basis of the amino acid sequence of a peptide resulting from trypsin digestion of purified GA$_{12}$ 20-oxidase from C. maxima endosperm [see SEQ ID NO 7].

An oligo(dT)-primed cDNA library was constructed in λgt11 (Amersham) using cotyledon mRNA. The total library (70,000 clones) was amplified to give 3.6×10$^8$ plaque forming units (pfu)/ml of which 69% were recombinant. Immunoscreening of the amplified library was performed with 3,600 pfu on one 90 mm plate and probing with the 20-oxidase peptide antibody (1 mg/ml) and an alkaline phosphatase-conjugated anti-rabbit IgG second antibody.

Seven positive plaques were obtained and these, as well as one negative plaque as control, were replated at 50 pfu/plate and rescreened. Nine positive plaques from one plate were assayed for GA$_{12}$ 20-oxidase activity by incubating agar plugs (ca 5 ml) in Eppendorf tubes containing $[^{14}C]$ GA$_{12}$ and co-factors as given in Example 1 in 25 ml SM buffer. Incubations were for 6 h, replenishing the co-factors every 2 h. Products were recovered after centrifugation (15,000 g for 2 min) and separated by reverse-phase HPLC connected on-line to a radioactivity monitor.

All plaques were active giving up to 60% conversion of substrate to [$^{14}$C] $GA_{15}$. Similarly, two positive plaques chosen from each of the remaining plates also expressed functional protein; in this case by taking larger (ca 25 ml) agar plugs the substrate was completely converted to mainly $GA_{24}/GA_{25}$. No positives were obtained after replating a negative plaque and rescreening with the antibody and two plaques from this plate chosen at random possessed no $GA_{12}$ 20-oxidase activity.

Positive plaques, after purification, converted [$^{14}$C] $GA_{12}$ to radiolabelled $GA_{15}$, $GA_{24}$ and $GA_{25}$ when agar plugs were incubated with the substrate and co-factors. Negative plaques contained no enzyme activity. The size of the inserts in the positive bacteriophages were shown using the polymerase chain reaction with λgt11 primers to be all about 1.4 kilobase pairs (kbp).

EXAMPLE 3

Metabolism of [$^{14}$C] GAs by Recombinant 20-oxidase

We examined the catalytic properties of the recombinant protein using a lysogen from a single bacteriophage.

Recombinant GA 20-oxidase was prepared from a λgt11 lysogen in Y1089 essentially as in Sambrook, J., Fritsch, E. F. & Maniatis, T. Molecular Cloning: A Laboratory Manual 2nd edn (Cold Spring Harbor Laboratory Press, New York; 1989), but using a lysogen extraction buffer containing 200 mM Tris-HCl, pH 7.0 and 8 mM dithiothreitol. The activity of the protein was examined by incubating cell lysates with GA precursors. The capacity of the protein to oxidise [$^{14}$C] $GA_{12}$ was absolutely dependent on the addition of 2-oxoglutaric acid and was reduced by 73 and 90%, respectively, when $Fe^{2+}$ or ascorbic acid were omitted.

The substrate specificity of the protein was also determined (Table 1). Different aliquots of the cell lysates were incubated with 100,000 dpm [$^{14}$C] $GA_{12}$ (A) or [$^{14}$C] $GA_{53}$ (B) and co-factors as described in Example 1 in a total volume of 250 ml for 4 h at 30° C., with fresh co-factors added after 2 h. In C, the substrates (200,000 dpm) were incubated with 250 ml of the lysate with co-factors for 6 h, replenishing the co-factors every 2 h. Products were extracted and analysed by HPLC-radiocounting and their identity confirmed by combined gas chrmatography-mass spectrometry (GC-MS). The specific radioactivities of products and substrates were the same. The results are shown in Table 1.

TABLE 1

A. Incubations with [$^{14}$C] $GA_{12}$

| A | Products (%) | | |
|---|---|---|---|
| Supernatent (ml) | $GA_{12}$ | $GA_{15}$ | $GA_{24}/GA_{25}$* |
| 1.0 | 48 | 49 | 3 |
| 2.0 | 10 | 70 | 20 |
| 3.9 | 3 | 14 | 84 |
| 7.8 | 4 | 4 | 92** |

B. Incubations with [$^{14}$C] $GA_{53}$

| | Products (%) | | | | |
|---|---|---|---|---|---|
| Supernatant (ml) | $GA_{53}$ | $GA_{44}$ | $GA_{19}$ | $GA_{17}$ | $GA_{20}$... |
| 7.8 | 42 | 58 | 0 | 0 | 0 |
| 15.6 | 13 | 79 | 8 | 0 | 1 |
| 31.3 | 1 | 69 | 25 | 5 | 1 |
| 62.5 | 0 | 49 | 39 | 10 | 2 |
| 125 | 0 | 29 | 46 | 23 | 2 |
| 250 | 0 | 16 | 43 | 38 | 2 |

C. Incubations with 20-oxo-[$^{14}$C] GAs

| Substrate | Products (%) | |
|---|---|---|
| $GA_{24}$ | $GA_{25}/GA_9(96)$* | |
| $GA_{19}$ | $GA_{17}(49)$ | $GA_{20}(0.9)$ |
| $GA_{23}$ | $GA_{28}(3.4)$*** | $GA_1(0.4)$ |

*Not resolved by HPLC.
**Shown by GC-MS to contain only [$^{14}$C] $GA_{25}$
***Identity of [$^{14}$C] GA was not confirmed by GC-MS.

When the protein was incubated at increasing concentrations with [$^{14}$C] $GA_{12}$ (Table 1A) sequential oxidation of the C-20 methyl group to the alcohol aldehyde and carboxylic acid occurred to give, respectively, radiolabelled $GA_{15}$, $GA_{24}$ and $GA_{25}$ as products. The corresponding 13-hydroxy GA products ($GA_{44}$, $GA_{19}$ and $GA_{17}$) were also obtained, although at lower efficiency, when the lysate was incubated with [$^{14}$C] $GA_{53}$ (Table 1B). A comparison of the aldehyde substrates $GA_{24}$ (non-hydroxylated), $GA_{19}$ (monohydroxylated) and $GA_{23}$ (dihydroxylated), showed that the efficiency of oxidation to the corresponding tricarboxylic acids decreased with increasing polarity of the substrate (Table 1C). In addition, the corresponding $C_{19}$-GA products ($GA_9$, $GA_{20}$ and $GA_1$), which are formed by loss of C-20 as $CO_2$, were obtained in low yield. The results indicate that a single enzyme may catalyse each of the steps involving oxidation at C-20 during GA biosynthesis, possibly also including the loss of C-20, although confirmation of this must await studies with the corresponding enzyme from a plant tissue in which $C_{19}$-GA production forms a major pathway.

EXAMPLE 4

Nucleotide Sequence of GA 20-oxidase cDNA Clone and Derived Amino Acid Sequence Restriction analysis of PCR-amplified bacteriophage inserts indicated the presence of an internal EcoRI site, but no internal BamHI sites. Bacteriophage DNA was prepared after infection of E. coli strain Y1090 (Amersham; 400 ml culture) and purified using a Lambda Phage Purification kit (Qiagen). After release of the insert with BamHI it was subcloned by insertion into the BamHI site of pUC18 and transformation of E. coli strain XL1blue. Plasmids were isolated from the transformants (Qiagen Plasmid Midi Kit) and one was sequenced on both strands by the dideoxynucleotide chain termination method.

The selected clone has been deposited as pB11 (E. coli) with the Agricultural Research Service Culture Collection (NRRL), Northern Regional Research Centre, 1815 North University Street, Peoria, Ill. 61604. The accession number is NRRL B-21096 and the deposition date is May 21, 1993.

The nucleotide sequence of the selected clone contains an open reading frame of 1,158 nucleotides encoding a protein of Mr 43,321, which agrees closely with the value determined for the native enzyme.

The sequence contains regions of homology with those of previously cloned plant dioxygenases, including flavanone 3-hydroxylase, hyoscyamine 6-hydroxylase, E8, a ripening related gene of unknown function, and 1-aminocyclopropane-1-carboxylic acid oxidase, an enzyme involved in the production of the plant hormone ethylene. The conserved sequences include three histidine-containing motifs, two of which have been proposed as Fe-binding sites at the enzyme active centre. Amino acids that are conserved in other plant dioxygenases are shown in bold type.

The sequence of the peptide against which the antibody for screening the expression library was raised is present close to the N-terminus and is underlined. It has one difference (P for V), which we found subsequently to be due to an impurity in the tryptic peptide that was sequenced. Thus, all clones selected using this antibody would be near full-length and, as we have demonstrated, should encode functional proteins.

Heterologous Expression of the Pumpkin GA 20-oxidase in *E. coli*

When the cDNA insert from pB11, encoding GA 20-oxidase from pumpkin, is expressed in *E. coli*, the protein produced catalyses the successive oxidation of the C-20 methyl group. Only 1% of the products are biologically active C19-gibberellins; formed by loss of C-20 as $CO_2$; 99% of the products have a carboxylic acid group at C-20 and are not biologically active, nor can be converted to active gibberellins. Production of this enzyme in plants should, therefore, divert the $C_{20}$-gibberellin intermediates of GA biosynthesis (mainly $GA_{12}$ and $GA_{53}$) to the carboxylic acid forms, so reducing the levels of active GAs.

EXAMPLE 5

Construction of a 35S-GA 20 Chimaeric Gene (the GA20 cDNA Cloned into pCGN1761)

GA20 oxidase is expressed in sense and antisense behind the constitutive 35S promoter. The cDNA encoding the GA20 oxidase gene is transferred to the vector pCGN1761 which carries the double 35S CaMV promoter and the tml transcriptional terminator on a pUC-derived plasmid The construction of pCGN1761 is disclosed in example 23 on pages 39 to 41 of EP-A 0 392 225, which is incorporated herein by reference. The 1.4 BamHI fragment containing the GA20 oxidase gene is excised from the pUC-based plasmid described in example 4 and ligated to an annealed molecular adaptor of the sequence 5'-AATTCGAACCCCTTCG-3' (SEQ ID NO: 18)/5'-GATCCGAAGGGGTTCG-3' (SEQ ID NO: 19) (New England Biolabs #1105 and #1106), thus converting the BamHI ends to EcoRI ends. The ligation product is purified and cloned into the EcoRI site of pCGN1761 using standard techniques. Colonies carrying the cDNA in sense and antisense orientations relative to the double 35S promoter are recovered and are named pCGN1761-35S-GA20ox-A and pCGN1761-35S-GA20ox-B respectively.

EXAMPLE 6A

Transfer of the 35S-GA 20 Fusion From pCGN1761-35S-GAox-A and pCGN1761-35S-GAox-B to the Binary Vector pCIB2001

The 35S-GA20 expression cassette is excised from constructions pCGN1761-35S-GAox-A and pCGN1761-35S-GAox-B described above by firstly cutting with HindIII, rendering the linearized plasmid blunt by incubation with T4 DNA polymerase, and then cutting with HpaI to release the 35S-GA20-tml insert. This is cloned into the StuI site of pCIB2001 generating binary vectors expressing the GA20ox gene in sense and antisense orientation behind the double 35S promoter.

EXAMPLE 6B

Transfer of the 35S-GA 20 Fusion From pCGN1761-35S-GAox-A and pCGN1761-35S-GAox-B to the Direct Gene Transfer ector pCIB3064

The 35S-GA20 expression cassette is excised from constructions pCGN1761-35S-GAox-A and pCGN1761-35S-GAox-B described in example 5 by firstly cutting with HindIII, rendering the linearized plasmid blunt by incubation with T4 DNA polymerase, and then cutting with HpaI to release the 35S-GA20-tml insert This fragment is cloned into the HindIII site (rendered blunt by incubation with T4 DNA polymerase) of pCIB3064 [Koziel et al (1993)] generating vectors for direct gene transfer, utilizing PAT-gene selection, expressing the GA20ox gene in sense and antisense orientation behind the double 35S promoter.

EXAMPLE 7

Construction of a PR1-GA 20 Chimaeric Gene (the GA20 cDNA Cloned into pCIB 1004)

The cDNA encoding the GA20 oxidase gene is transferred to the vector pCIB1004 to place it under the control of the chemically inducible PR1a gene promoter. pCIB1004 is cleaved with NcoI and the 3' overhang is rendered blunt by incubation with T4 DNA polymerase. The construction of pCIB1004 is disclosed in example 21B on page 36 of EP-A 0 332 104, which is incorporated herein by reference. Subsequently BamHI non-phosphorylated linkers (New England Biolabs #1003) are ligated to the termini, and cleavage with BamHI releases an insert which is discarded. The 1.4 A kb GA20-containing gene is excised from the construction of example 4 by cleavage with BamHI, and ligated to the BamHI site of the pCIB1004-derived fragment thus fusing the GA20 gene to the PR1a promoter in both orientations. The resultant plasmids are termed pCIB1004-PR1-GA20ox-A (sense orientation and pCIB1004-PR1-GA20ox-B (antisense orientation).

EXAMPLE 8A

Transfer of the PR1-GA20 Fusion From pCGN1004-PR1-GAox-A and pCGN1004PR1-GAox-B to the Binary Vector pCIB2001

The PR-GA20 expression cassette is transferred from the pCIB1004-derived construct by partial digestion with KpnI, recovery of a fragment of 5.6 kb in size, and ligation of this fragment into the KpnI site of pCIB2001. This generates binary vectors carrying the GA20ox gene for expression behind the chemically regulated PR1a promoter in sense and antisense orientations.

EXAMPLE 8B

Transfer of the PR1-GA20 Fusion From pCGN1004-PR1-GAox-A and pCGN1004-PR1-GAox-B to the Direct Gene Transfer Vector pCIB3064

The PR-GA20 expression cassette is transferred from the pCIB1004-derived construct (example 7) by partial digestion with KpnI, recovery of a fragment of 5.6 kb in size, incubation with T4 DNA polymerase to render termini blunt, and ligation of this fragment into the HindIII site (rendered blunt by incubation with T4 DNA polymerase) of pCIB3064 generating vectors for direct gene transfer, utilizing PAT-gene selection, expressing the GA20ox gene in sense and antisense orientation behind the chemically regulated PR1a promoter.

EXAMPLE 9

Construction of a Pth-GA 20 Chimaeric Gene

A pith-specific promoter from maize is used to express the GA20 gene in sense and antisense orientation in a tissue-specific manner. pCGN1761 is cleaved with XhoI and SalI and treated with T4 DNA polymerase to render termini blunt. The larger of the two resultant fragments is gel purified. A BamHI fragment carrying a pith-specific promoter is excised from the plasmid pCIB4433 (WO 93/07278) and ligated to the 1.4 kb fragment carrying the GA20-oxidase gene. Plasmid pCIB4433 has been deposited with the Agricultural Research Culture Collection (NRRL) (1818 N. University SL, Ill. 61604) under the provisions of the Budapest Treaty under the Deposition No NRRL B-18999 on Sep. 21, 1992. Following ligation, the mixture is treated with T4 DNA polymerase and the resultant blunt fragments are ligated into the pCGN1761-derived fragment. By restriction mapping and sequence analysis of the *E. coli* clones obtained it is possible to identify clones oriented with the Pth promoter driving expression of the sense GA20 gene upstream of the tml transcription terminator, and clones oriented with the Pth promoter driving expression of the GA20 gene in antisense orientation, upstream of the tml terminator. These clones are designated pCGN1761-Pth-GA20ox-A and pCGN1761-Pth-GA20ox-B respectively.

EXAMPLE 10A

Transfer of the pepC-GA20 Fusion From pCGN1761-PepC-GAox-A and pCGN1761-PepC-GAox-B to the Binary Vector pCIB2001

The Pth-GA20ox cassette is excised from pCGN1761-Pth-GA20ox-A and pCGN1761-Pth-GAox-B using BglII and HpaI and cloned into the corresponding sites in pCIB2001. This generates binary vectors with GA20ox cloned in sense and antisense orientation under the regulation of the pith specific Pth promoter.

EXAMPLE 10B

Transfer of the PepC-GA20 Fusion From pCGN1761-PepC-GAox-A and pCGN1761-PepC-GAox-B to the Direct Gene Transfer Vector pCIB3064

The Pth-GA20ox cassette is excised from pCGN1761-Pth-GA20ox-A and pCGN1761-Pth-GAox-B by firstly cutting with BglII, rendering the linearized plasmid blunt by treatment with T4 DNA polymerase, and then cutting with HpaI to release the Pth-GA20ox insert. This is cloned into the HindIII site (rendered blunt by incubation with T4 DNA polymerase) of pCiB3064 generating vectors for direct gene transfer, utilizing PAT-gene selection, expressing the GA20ox gene in sense and antisense orientation under the regulation of the pith specific Pth promoter.

EXAMPLE 11

Construction of the Binary Vector pCIB2001

TJS75 Kan is first created by digestion of pTJS75 [Schmidhauser et al, J Bacteriol 164: 446455, 1985] with NarI to excise the tetracycline gene, followed by insertion of an AccI fragment from pUC4K [Messing et al, Gene 19: 259–268, 1982] carrying a Npt I gene. pCIB 200 is then made by ligating XhoI linkers to the EcoRV fragment of pCIB7 (containing the left and right T-DNA borders, a plant selectable nos/nptII chimaeric gene and the pUC polylinker, [Rothstein et al, Gene 53: 153–161, 1987] and cloning XhoI digested fragment into salI digested TJS75 Kan. pCIB2001 is made by cloning a new polylinker into the multiple cloning site of pCIB200 to give more unique restriction enzyme sites.

PLANT TRANSFORMATION

The recombinant DNA according to the invention comprising the GA20 oxidase encoding DNA sequence can be introduced into the plant cell using one of the well established Agrobacterium transformation systems or by means of direct gene delivery comprising, for example, microinjection [Crossway et al (1986); Neuhaus (1987)], electroporation [Riggs et al (1986)], direct gene transfer [Paszkowski et al, (1984)], or ballistic particle acceleration using, for example, devices available from Agracetus, Inc., Madison, Wis. and Dupont, Inc., Wilmington, Del.

The detection of transformed plant cells may be accomplished using suitable selection systems well known in the art. A suitable selection marker gene may be present in the plant expression vector used in plant transformation or may alternatively be provided on one of the conventionally applied selection plasmids such as that described by Rothstein et al (1987) containing a selectable hygromycin resistance gene. The said plasmid may be introduced into the plant cell together with the recombinant DNA according to the invention comprising the GA20 oxidase encoding DNA sequence using co-transformation.

EXAMPLE 12

*A. tumefaciens*-mediated Transformation of *N. tabacum*

Explants roughly 5 to 10 mm are cut from young leaves 3 to 5 cm long and third to sixth from the apex of *N. tabacum* cv 'Xanthi nc' grown under axenic conditions [Facciotti and Pilet, 1979] in solid MS medium [Murashige and Skoog, 1962] containing 0.7% phytagar (Gibco-BRL), 1 mg/l IAA, 0.15 mg/l kinetin. These explants are plated on solid MS medium containing 0.6% phytagar, 40 mg/l adenine sulfate, 2 mg/l IAA, and 2 mg/l kinetin on the surface of which is placed a #1 Whatman filter and incubated for 24 hr in the dark at 24 C. Agrobacterium strains containing the binary vectors described above are grown overnight in LBMG at 30 C. on a shaker at 180 rpm. Explants are dipped into a bacterial suspension of $3.3 \times 10^8$ cells/ml for approximately 5 minutes, blotted on sterile paper towels, and re-plated on the same plates. After 48 hours explants are placed on selection medium containing the same plate medium as above plus 350 mg/l cefotaxime and 100 mg/l kanamycin. Co-cultivated control tissue is placed on the same medium but without kanamycin. The explants are transferred to fresh media every two weeks. Shoots are harvested 4 to 8 weeks after co-cultivation, placed on 50 ml culture tubes with 25 ml of solid MS medium containing 0.6% phytogar, 1 mg/l IBA, 350 mg/l cefotaxime, and 100 mg/l kanamycin. All tissue is grown at 24 C. to 28 C., 12 hours of light, 12 hours dark, light intensity 6700 to 8400 lx. Shoots root in 1 to 2 weeks and are then transplanted to planting mix in 4" pots and placed in the "transgenic plant phytotron".

EXAMPLE 13

Leaf Disk Transformation of Tobacco

Agrobacterium Strains containing the binary vectors described above are grown 18 to 24 hours in glutamate salts media adjusted to pH 5.6 and supplemented with 0.15% mannitol, 50 mg/ml kanamycin, 50 mg/ml spectinomycin and 1 mg/ml streptomycin before they are diluted to an $OD_{600}$ of 0.2 in the same media without the antibiotics. The bacteria are then grown for three to five hours before dilution to an $OD_{600}$ of 0.2 to 0.4 for inoculation of discs of 5 to 7 mm punched from leaves of *N. tabacum* cv xanthi that have been grown aseptically in GA7 containers, following a modification of the methods of Horsch et al (1985).

The leaf disks are maintained on 0.7% agar containing Murashige and Skoogs major and minor salts (MS), 1 mg/l benzyladenine and 1 mg/ml NAA for two days before transfer to the same media containing 50 mg/ml kanamycin, 100 mg/ml carbenicillin and 100 mg/ml mefoxin. Shoots which form on the disks are excised and propagated until six plantlets are obtained by subculturing the shoot tips on MS media containing 50 mg/ml kanamycin in GA7 containers.

The plantlets are rooted on medium containing no hormones and 50 mg/ml kanamycin, transferred to soil and hardened in a phytotron before transfer to the greenhouse for induction treatment with chemical regulators. At flowering time flowers are induced to selfpollinate. Seeds are harvested following maturation.

EXAMPLE 14

Production of Transgenic Tobacco Callus and Plants

Agrobacterium strains containing the binary vectors described above are used to transform callus forming from leaf disks. Callus forming on kanamycin-containing MSBN selection medium is maintained on a callus growth medium comprised of MS major, minor salts and Fe-EDTA (Gibco #500-1117; 4.3 g/l), MS vitamins, 100 mg/l myo-inositol, 20 g/l sucrose, 2 mg/l NAA and 0.3 mg/l kinetin.

The callus can be used to regenerate transgenic plants by transferring callus pieces to MSBN medium and following methods described.

EXAMPLE 15

Transformation of Carrot

Agrobacterium strains containing the binary vectors described above are grown as described in Example 13. The bacteria, diluted to an $OD_{600}$ of 0.2 to 0.4, are then used for inoculation of discs cut from surface sterilized carrots.

To surface sterilize the carrots they are peeled and then soaked 20 minutes in a 10% solution of chlorox. The carrots are rinsed with sterile water, sliced into 5 mm pieces and placed basal side up onto water agar. 20 to 50 ml of bacteria are then applied to the upper surface of the disks. After 7 days the disks are transferred to 0.7% agar containing MS salts, 3% sucrose, 0.1 mg/l 2,4-D, 50 mg/ml kanamycin, 100 mg/ml carbenicillin, and 100 mg/ml mefoxin. Callus forming around the cambial ring is excised and placed on 0.7% MS agar supplemented with 3% sucrose 0.1 mg/l 2,4-D, 50 mg/ml kanamycin, 100 mg/ml carbenicillin, and 100 mg/ml mefoxin. After the callus has been grown it is cut into small pieces and randomized onto four plates of the same media.

EXAMPLE 16

Transformation of Sunflower

Agrobacterium strains containing the binary vectors described above are grown as described. The bacteria, diluted to an $OD_{600}$ of 0.2 to 0.4, are then used for inoculation of stems of sunflower plants prepared as follows:

Sunflower seeds are soaked 10 mins in 10% captan followed by 10 mins in 10% chlorox and rinsing with sterile water. The seed coats are removed and the seeds are germinated on 0.7% water agar in the dark for three days, after which they are placed into a labline incubator set at 23 C. with a 12 hour day and night. The seedlings are grown for one week before decapitation and inoculation of the bacteria onto the cut stem surface.

After one week the inoculated stems are cut and placed on 0.7% agar containing MS salts, 3% sucrose, 2 mg/ml NAA, 1 mg/ml BAP, 100 mg/ml carbenicillin, 100 mg/ml mefoxin and 50 mg/ml kanamycin. The callus is transferred to fresh media every two weeks until sufficient quantity is obtained for 4 plates. Half of the callus growing from the virulent Agrobacterium strains is transferred to media without hormones containing 50 mg/ml kanamycin.

EXAMPLE 17

Transformation of Tomato

Agrobacterium strains containing the binary vectors described above are grown as described in Example 13. The bacteria, diluted to an $OD_{600}$ of 0.2 to 0.4, are then used for inoculation of stems of tomato seedlings prepared as follows:

Tomato seeds are soaked 20 mins in 10% chlorox and rinsed with sterile water. The seeds are germinated on 0.7% water agar in the dark for three days, after which they are placed into a labline incubator set at 23 C. with a 12 hour day and night. The seedlings are grown for one week before decapitation and inoculation of the bacteria onto the cut stem surface.

After one week, the inoculated stems are cut and placed on 0.7% agar containing MS salts, 3% sucrose, 2 mg/ml NAA, 1 mg/ml BAP, 100 mg/ml carbenicillin, 100 mg/ml mefoxin and 50 mg/ml kanamycin. The callus is transferred to fresh media every two weeks until sufficient quantity is obtained for 4 plates.

EXAMPLE 18

Transformation of Cotton

Agrobacterium strains containing the binary vectors described above are grown as described. The bacteria, diluted to an $OD_{600}$ of 0.2 to 0.4, are then used for inoculation of cotton cotyledons prepared as follows:

The cotton seeds are soaked 20 mins in 10% chlorox and rinsed with sterile water. The seeds are germinated on 0.7% water agar in the dark. The seedlings are grown for one week before inoculation of the bacteria onto the cotyledon surface. The inoculated cotyledons are allowed to form a callus before they are cut and placed on 0.7% agar containing MS salts, 3% sucrose, 100 mg/ml carbenicillin, and 100 mg/ml mefoxin. The callus is transferred to fresh media every three weeks until sufficient quantity is obtained for 4 plates. Half of the callus growing from the virulent Agrobacterium strains is transferred to media without hormones containing 50mg/ml kanamycin.

EXAMPLE 19

Preparation of a Special Type of Callus of *Zea mays*, Elite Inbred line Funk 2717

ZeaAmays plants of the inbred line Funk 2717 are grown to flowering in the greenhouse, and self pollinated. Immature ears containing embryos approximately 2 to 2.5 mm in length are removed from the plants and sterilized in 10% chlorox solution for 20 minutes. Embryos are aseptically removed from the kernels and plated with the embryo axis downwards on OMS medium containing 0.1 mg/l 2,4-D, 6% sucrose and 25 mM L-proline solidified with 0.24% Gelrite$^R$ (initiation medium). After two weeks' culture in the dark at 27 C., the callus developing on the scutellum is removed from the embryo and plated on B5 medium (Gamborg et al, 1968) containing 0.5 mg/l 2,4-D and solidified with 0.24% Gelrite$^R$. The callus is subcultured every two weeks to fresh medium. After a total of eight weeks after placing the embryos on the initiation medium, the special type of callus is identified by its characteristic morphology. This callus is subcultured further on the same medium. After a further period of two months, the callus is transferred to, and serially subcultured on N6 medium containing 2 mg/l 2,4D and solidified with Gelrite$^R$.

EXAMPLE 20

Preparation of a Suspension Culture of *Zea mays*, Elite Inbred Funk 2717

The callus described above is subcultured for a total of a least six months. The type of callus chosen for subculture is relatively non-mucilaginous, granular and very friable, such that it separates into small individual cell aggregates upon placing into liquid medium. Cultures containing aggregates with large, expanded cells are not retained. Approximately 500 mg aliquots of the special callus of *Zea mays* elite inbred funk 2717 are placed into 30 ml of N6 medium containing 2 mg/l 2,4-D in 125 ml Delong flasks. After one week of culture at 26 C. in the dark on a gyratory shaker (130 rpm, 2.5 cm throw), the medium is replaced with fresh medium. The suspensions are again subcultured in this way after another week. At that time, the cultures are inspected, and those which do not show large numbers of expanded cells are retained. Suspension cultures containing aggregates with large, expanded cells are discarded. The preferred tissue consists of densely cytoplasmic dividing cell aggregates which have a characteristically smoother surface that the usual type of cell aggregates. The cultures retained have at least 50% of the cells represented in these small aggregates. This is the desired morphology. These suspensions also have a rapid growth rate, with a doubling time of less than one week. The suspension cultures are subcultured weekly by transferring 0.5 ml PCV into 25 ml of fresh medium. After four to six weeks of subculture in this fashion, the cultures increase two- to threefold per weekly subculture. Cultures in which more than 75% of the cells are of the desired morphology are retained for further subculture. The lines are maintained by always choosing for subculture the flash whose contents exhibit the best morphology. Periodic filtration through 630 mm pore size stainless steel sieves every two weeks is used in some cases to increase the dispersion of the cultures, but is not necessary.

EXAMPLE 21

Preparation of Protoplasts from Suspension Cultures of *Zea mays*

1 to 1.5 ml PCV of the suspension culture cells from above are incubated in 10 to 15 ml of a filter-sterilied mixture consisting of 4% cellulase RS with 1% Rhozyme in KMC (8.65 g/l KCl, 16.47 g/l MgCl$_2$.6H$_2$O and 12.5 g/l CaCl$_2$.2H$_2$O, pH 5.6) salt solution. Digestion is carried out at 30 C. on a slow rocking table for a period of 3 to 4 hours. The preparation is monitored under an inverted microscope for protoplast release. The protoplasts which are released are collected as follows:

The preparation is filtered through a 100 mm mesh sieve, followed by a 50 mm mesh sieve. The protoplasts are washed through the sieves with a volume of KMC salt solution equal to the original volume of enzyme solution. 10 ml of the protoplast preparation is placed in each of several disposable plastic centrifuge tubes, and 1.5 to 2 ml of 0.6 M sucrose solution (buffered to pH 5.6 with 0.1% MES and KOH) layered underneath. The tube is centrifuged at 60 to 100×g for 10 minutes, and the protoplasts banding at the interface collected using a pipette and placed in a fresh tube. The protoplast preparation is resuspended in 10 ml of fresh KMC salt solution, and centrifuged for five minutes at 60 to 100×g. The supernatant is removed and discarded, and the protoplasts resuspended gently in the drop remaining, and then 10 ml of a $13/14$ strength KMC solution gradually added. After centrifuging again for five minutes, the supernatant is again removed and the protoplasts resuspended in a $6/7$ strength KMC solution. An aliquot is taken for counting, and the protoplasts again sedimented by centrifugation. The protoplasts are resuspended at $10^7$ per ml in KM-8p medium or in 0.5 M mannitol containing 6 mM MgCl$_2$ or other suitable medium for use in transformation as described in the following examples. This protoplast suspension is used for transformation and is cultured as described below.

EXAMPLE 22

Transformation of *Zea mays* Protoplasts by Electroporation

A. All steps except the heat shock are carried out at room temperature (22 to 28 C.). The protoplasts are resuspended in the last step of above in 0.5 M mannitol containing 0.1% MES and 6 mM MgCl$_2$. The resistance of this suspension is measured in the chamber of a Dialog Electroportor and adjusted to 1 to 1.2 kL using a 300 mM MgCl$_2$ solution. The protoplasts are heat-shocked by immersing the tube containing the sample in a water bath at 45 C. for five minutes, followed by cooling to room temperature on ice, 4 mg of linearized plasmid and 20 mg of calf thymus carrier DNA are added to aliquots of 0.25 ml of this suspension. 0.125 ml of a 24% PEG solution (MW8000) in 0.5 M mannitol containing 30 mM MgCl$_2$ are added to the protoplasts. The mixture is mixed well but gently, and incubated for 10 minutes. The sample is transferred to the chamber of the electroporator and samples pulsed three times at 10 second intervals, at initial voltages of 1500, 1800, 2300 or 2800 Vcm$^{-1}$, and an exponential decay time of 10 msec.

The protoplasts are cultured as follows. The samples are plated in 6 cm petri dishes at room temperature. After a further 5 to 15 minutes, 3 ml of KM-8p medium containing 1.2% SeaPlaque agarose and 1 mg/l 2,4-D are added. The agarose and protoplasts are mixed well and the medium allowed to gel.

B. This is repeated with one or more of the following modifications:

The resistance of the protoplast preparation is adjusted to 0.5 to 0.7 kL.

The PEG used is PEG with a MW of 4000. No PEG is added, or one-half volume of 12% PEG is added.

The pulses are applied at intervals of three seconds.

The protoplasts are plated after the electroporation in dishes placed on a plate cooled to a temperature of 16 C.

The protoplasts are placed in tubes after the electroporation step, washed with 10 ml of $6/7$ strength KMC solution or with W5 solution (comprised of 380 mg/KCl, 18.375 g/l $CaCl_2.2H_2O$, 9 g/l NaCl; 9 Ag/l glucose, pH 6.0), then collected by centrifugation at 60×g for 10 minutes, resuspended in 0.3 ml of KM medium and plated as in A.

The calf thymus carrier DNA is not added.

EXAMPLE 23

Transformation of *Zea mays* Protoplasts by Treatment with PEG

A. The protoplasts are resuspended at the last step of above in a 0.5 M mannitol solution containing 12 to 30 mM $MgCl_2$. A heat shock of 45° C. for five minutes is given as described. The protoplasts are distributed in aliquots for transformation in centrifuge tubes, 0.3 ml of suspended protoplasts per tube. During the next 10 minutes the following are added: DNA and PEG solution (MW 6000, 40% containing 0.1 M $Ca(NO_3)_2$ and 0.4 M mannitol; pH 8 to 9 with KOH) to give a final concentration of 20% PEG. The aliquots are incubated for 30 minutes with occasional gende shaking, and then the protoplasts are placed in petri dishes (0.3 ml original protoplast suspension per 6 cm diameter dish) and cultured as described.

B. This is repeated and the protoplasts are washed after 30 minutes of incubation in the PEG solution of above, by adding 0.3 ml of W5 solution five times at two- to three-minute intervals. The protoplast suspension is centrifuged, the supernatant removed, and the protoplasts are cultured as described.

C. The above is repeated with the modification that the final concentration of PEG is between 13 and 25%.

EXAMPLE 24

Regeneration of Callus From Protoplasts

The plates containing the protoplasts in agarose are placed in the dark at 26° C. After 14 days, colonies arise from the protoplasts. The agarose containing the colonies is transferred to the surface of a 9 cm diameter petri dish containing 30 ml of N6 medium containing 2 mg/l 2,4-D, solidified with 0.24% Gelrite. This medium is referred to as 2N6. The callus is cultured further in the dark at 26° C. and callus pieces subcultured every two weeks onto fresh solid 2N6 medium.

EXAMPLE 25

Selection of Transformed Callus of *Zea mays*

The above example is repeated with the modification that an appropriate selection agent is added to the 2N6 medium in order to select for transformed cells.

EXAMPLE 26

Regeneration of Corn Plants

A. Callus is placed on 2N6 medium for maintenance and on ON6 (comprising N6 medium lacking 2,4-D) and N61 medium (comprising N6 medium containing 0.25 mg/l 2,4-D and 10 mg/l kinetin) to initiate regeneration. Callus growing on ON6 and N61 media is grown in the light (16 hours/day light of 840 to 8400 Ix from white fluorescent lamps). Callus growing on N61 medium is transferred to ON6 medium after two weeks, as prolonged time on N61 medium is detrimental. The callus is subcultured every two weeks even if the callus is to be transferred again on the same medium formulation. Plantlets appear in about four to eight weeks. Once the plantlets are at least 2 cm tall, they are transferred to ON6 medium in GA7 containers. Roots form in two to four weeks, and when the roots look well-formed enough to support growth, the plantlets are transferred to soil in peat pots, under a light shading for the first four to seven days. It is often helpful to invert a clear plastic cup over the transplants for two to three days to assist hardening off. Once the plants are established, they are treated as normal corn plants and grown to maturity in the greenhouse. In order to obtain progeny plants are self pollinated or crossed with wild type.

B. The above example is repeated with the modification that an appropriate selection agent is added to the medium used to maintain the callus.

EXAMPLE 27

Production of Transgenic Maize Plants

Tissue

Immature maize embryos, approximately 1.5–2.5 mm in length, are excised from an ear of genotype 6N615 14–15 days after pollination. The mother plant is grown in the greenhouse. Before excision, the ear is surface sterilized with 20% Clorox for 20 minutes and rinsed 3 times with sterile water. Individual embryos are plated scutellum side in a 2 cm square area, 36 embryos to a plate, on the callus initiation medium, 2DG4+5 chloramben medium (N6 major salts, B5 minor salts, MS iron, 2% sucrose, with 5 mg/l chloramben, 20 mg/l glucose, and 10 ml G4 additions Table 1) added after autoclaving.

G4 Additions
Ingredient per liter medium
Casein hydrolysate 0.5 g
Proline 1.38 g
Nicotinic acid 0.2 mg
Pyridoxine-HCl 0.2 mg
Thiamine-HCl 0.5 mg
Choline-HCl 0.1 mg
Riboflavin 0.05 mg
Biotin 0.1 mg
Folic acid 0.05 mg
Ca pantothenate 0.1 mg
p-aminobenzoic acid 0.05 mg
B12 0.136 g Bombardment Tissue is bombarded using the PDS-1000He Biolistics device. The tissue is placed on the shelf 8 cm below the stopping screen shelf. The tissue is shot one time with the DNA/gold microcarrier solution, 101 dried onto the microcarrier. The stopping screen used is hand punched using 10×10 stainless steel mesh screen. Rupture discs of 1550 psi value are used. After bombardment, the embryos are cultured in the dark at 25 C.

Preparation of DNA for Delivery

The microcarrier is prepared essentially according to the instructions supplied with the Biolistic device.

Callus Formation

Embryos are transferred to callus initiation medium with 3 mg/l PPT 1 day after bombardment. Embryos are scored for callus initiation at 2 and 3 weeks after bombardment. Any responses are transferred to callus maintenance medium, 2DG4+0.5 2,4-D medium supplemented with an appropriate selection agent dependent on the selection marker gene used. Callus maintenance medium is N6 major salts, B5 minor salts, MS iron, 2% sucrose, with 0.5 mg/l 2,4-D, 20 mg/l glucose, and 10 ml G4 additions added after autoclaving. Embryogenic callus is subcultured every 2 weeks to fresh maintenance medium containing an appropriate selection agent. All callus is incubated in the dark at 25 C.

The Type I callus formation response is 18%. Every embryo which produced callus is cultured as an individual event giving rise to an individual line.

Regeneration

After 12 weeks on selection, the tissue us removed from callus maintenance medium with an appropriate selection agent and is placed on regeneration medium and incubated at 25 C. using a 16 hour light (50 E. m-2, s-1)/8 hour dark photoperiod. Regeneration medium is 0.25MS3S5BA (0.25 mg/l 2,4-D, S mg/l BAP, MS salts, 3% sucrose) for 2 weeks followed by subculture to MS3S medium for regeneration of plants. After 4 to 10 weeks, plants are removed and put into GA 7's.

EXAMPLE 28

Preparation of Embryogenic Suspensions from Tissue of *Dactylis glomerata* L. (Orchardgrass)

A. Embryogenic callus is initiated from basal sections of the youngest leaves of greenhouse-grown orchardgrass plants (*Dactylis glomerata* L.) as described by Hanning and Conger (1982). The leaves are surface sterilized by immersion in a 1:10 dilution of Chlorox solution (5.25% sodium hypochlorite; The Clorox Company, Oakland, Calif.) for about 10 minutes and then cut aseptically into small segments of 1 to 5 mm in length or in diameter. These segments are plated on sterile SH-30 medium containing 0.8% agarose as a gelling agent. Callus and/or embryogenic structures appear within 2 to 6 weeks after plating, upon culture at about 25° C. Embryogenic callus is maintained by subculturing onto fresh SH-30 medium every 2 to 4 weeks and culturing in the dark at 25° C.

B. Embryogenic suspension cultures are initiated by placing approximately 0.5 g fresh weight of embryogenic callus into 50 ml of liquid medium described by Gray and Conger (1985) containing 45 mM dicamba and 4 g/liter casein hydrolysate. The suspension cultures are grown at 27° C. under a 16 hours light (3300 lx), 8 hours dark photoperiod on a gyratory shaker at about 130 rpm in 125 ml Delong flasks sealed with a metal cap and paraffin. After approximately four weeks the large clumps are allowed to settle for about 30 seconds and 10 ml aliquots of the supernatant medium containing small cell clusters are removed and transferred to 50 ml of fresh medium. This process is repeated every 3 to 4 weeks using the most successful cultures as judged by smaller clump size and better quality based on the presence of small, cytoplasmic cells. After 5 to 8 transfers the suspensions are essentially free of non embryogenic cells and the majority of the embryogenic cell clusters are quite small (150 to 2000 mm).

EXAMPLE 29

Isolation and Purification of *Dactylis glomerata* L. Protoplasts

Protoplasts are prepared from embryogenic suspension cultures of above by aseptically filtering the cells on a Nalgene 0.2 mm filter unit and then adding 0.5 g fresh weight cells to each 12.5 ml of protoplasts enzyme mixture in a petri dish. The enzyme mixture consists of 2% Cellulase RS, 7 mM $CaCl_2xH_2O$, 0.7 mM $NaH_2PO_4xH_2O$, 3 mM MES (pH 5.6), glucose (550 mOs/kg $H_2O$ of pH 5.6), and is filter sterilized. The mixture is swirled on an orbital shaker at about 50 rpm in dim (<420 lx) light for about 4 to 5 hours. The digest is then sieved through a stainless steel sieve (100 mm mesh size) and distributed into 12 ml centrifuge tubes which are centrifuged at about 60 to 100×g for about 5 minutes. The protoplastcontaining sediment is then washed three times with protoplast culture medium KM-8p adjusted to 550 mOs/kg $H_2O$ with glucose. At this point a flotation step may be included for further purification of the protoplasts. In this case, the washed protoplasts are layered atop 10 ml of KM-8p culture medium adjusted to 700 mOs/kg $H_2O$ with sucrose. After centrifugation at 60 to 100×g for about 10 minutes, protoplasts banding at the interface are collected using a fine pipette. Finally, the protoplasts are resuspended in 1 to 2 ml KM-8p culture medium and sieved through a stainless steel screen (20 mm mesh size). The protoplasts released are collected and washed and resuspended in KM-8p medium for culture or in osmotically adjusted medium suitable for transformation according to the examples below.

EXAMPLE 30

*Dactylis glomerata* L. Protoplast Culture and Growth of Callus

A. The purified protoplasts are plated at a density of about $5×10^5$ protoplasts per ml in KM-8p culture medium containing 1.3% SeaPlaque agarose (FMC Corp., Marine Colloids Division, Rockland, Me., USA) and 30 to 40% of conditioned medium (obtained from 3 to 4 week-old *Dactylis glomerata* L. embryogenic suspension cultures by filtering the medium through a sterile Nalgene 0.2 mm filter, making the medium 550 mOs/kg $H_2O$ by addition of glucose, and again filter sterilizing). The plates are then placed in the dark at a constant temperature of 28° C. After 10 to 14 days the agarose is cut into wedges and placed into 'bead culture' as described by Shillito et al. (1983) using 20 ml SH-45 suspension culture medium with 3% sucrose per 3 ml original agarose embedded culture. The plants are put on a platform shaker and agitated at about 50 rpm in light at 670 lx. New suspension cultures are formed as the colonies grow out of the agarose and release cells into the liquid medium. The resultant suspension cultured cells are plated onto agar-solidified SH-30 medium and placed in the dark at 25° C. until callus is formed.

B. Protoplasts are cultured as described above except that the culture media contains no conditioned medium.

EXAMPLE 31

Transformation of *Dactylis glomerata* L. Protoplasts by Means of Electroporation A. Immediately after purification of the protoplasts, electroporation is performed according to Shillito et al. (1985) using linearized plasmid. The protoplasts are resuspended after the last wash at a density of about $7×10^6$ protoplasts per ml in the electroporation buffer (0.4 M mannitol, 6 mM $MgCl_2$). The protoplasts are placed in 0.7 ml aliquots in 10 ml plastic centrifuge tubes. Plasmid DNA and sonicated calf thymus DNA (Sigma) to give final concentrations of 10 mg/ml and 50 mg/ml respectively is added to the tubes. Then 0.38 ml PEG solution [24% PEG 6000 in 0.4 M mannitol, 30 mM $MgCl_2$, 0.1% MES (pH 5.6)] is added and the solution gently mixed. The protoplast suspension is transferred into the chamber of a Dialog Electroporator and 10 pulses of 3250 $Vcm^{-1}$ initial voltage and exponential decay constant of 10 msec applied at 30 sec intervals. The sample is removed from the chamber, and placed in a 10 cm diameter petri dish. 10 ml of KM-8p medium containing 1.2% SeaPlaque agarose is added, the protoplasts distributed evenly throughout the medium, and the agarose allowed to gel.

B. The above is repeated except that the initial voltage used is 3500 $Vcm^{-1}$, 4000 $Vcm^{-1}$, 5000 $Vcm^{-1}$, 3000 $Vcm^{-1}$, or 2500 $Vcm^{-1}$.

EXAMPLE 32

Transformation of *Dactylis glomerata* L. Protoplasts by Treatment with PEG

A. PEG mediated direct gene transfer is performed according to Negrutiu, I. et al., (1987). The DNA used is linearized plasmid described.

The protoplasts are suspended following the last wash in 0.5 M mannitol containing 15 mM $MgCl_2$ at a density of about $2\times10^6$ per ml. The protoplast suspension is distributed as 1 ml aliquots into 10 ml plastic centrifuge tubes. The DNA is added as described above, and then 0.5 ml of the PEG solution added (40% PEG 4000 in 0.4 M mannitol, 0.1 M $Ca(NO_3)_2$, pH 7.0).

The solutions are mixed gently and incubated for 30 minutes at room temperature (about 24° C.) for 30 minutes with occasional shaking. 1.4 ml of the wash solution is then added, and the contents of the tube gently mixed. The wash solution consists of 87 mM mannitol, 115 mM $CaCl_2$, 27 mM $MgCl_2$, 39 mM KCl, 7 mM Tris-HCl and 1.7 g/l myo-inositol, pH 9.0. Four further 1.4 ml aliquots of wash solution are added at 4 minute intervals, with mixing after each addition. The tube is then centrifuged at about 60×g for about 10 minutes, and the supernatant discarded. The sedimented protoplasts are taken up in 1 ml KM-8p culture medium, and placed in a 10 cm petri dish. 10 ml of KM-8p medium containing 1.2% SeaPlaque agarose is added. The protoplasts are evenly distributed throughout the medium and the agarose allowed to gel.

B. This is repeated with one or more of the following modifications:
(1) The pH of the wash solution is adjusted to 5.6 or 7.0.
(2) The PEG used is PEG of MW 6000, PEG of MW 2000 or PEG of MW 8000.
(3) The wash medium consists of 154 mM NaCl, 125 mM $CaCl_2$, 5 mM KCl, 5 mM glucose, pH to 6.0 with KOH, of 0.2 M $CaCl_2$, 0.1% MES, pH 6.0 with KOH, or of 0.2 M $CaCl_2$, 7 mM Tris/HCl, pH 9.0 with KOH.

EXAMPLE 33

Transformation of *Dactylis glomerata* L. Protoplasts by Electroporation or PEG Treatment Transformation is carried out as described above except that the protoplasts are treated at 45° C. for about 5 minutes prior to distribution of the aliquots into tubes for transformation or after distribution of the aliquots, and before addition of the PEG.

EXAMPLE 34

Selection of Transformed Colonies

A. The culture plates (petri dishes) containing the protoplasts are incubated for 10 days in the dark at about 25° C. and then cut into 5 equal slices for 'bead cultures' (Shillito et al., 1983). Four of the slices are placed each into 20 ml SH-45 culture medium containing 4 g/l casein hydrolysate and an appropriate selection agent dependent n the selection marker gene used in plant transformation. The fifth slice is put into 20 ml of the same medium but without selection agent as a non-selected control. After 4 to 5 weeks the putative transformed proptoplast-derived cell colonies growing in the presence of the selection marker are cut out of the agarose and placed into a 19 mm petri dish with 2 ml of liquid SH-45 medium containing an appropriate selection agent, which is agitated at about 50 rpm on a orbital shaker. After another 4 to 5 weeks all colonies which grow to make new suspensions are transferred into 125 ml Erlenmeyer flasks and grown in a manner similar to the parent suspension culture, except that an appropriate selection agent is included in the medium.

The new suspensions are subcultured every 1 to 3 weeks using SH-45 medium containing 4 g/l casein hydrolysate and an appropriate selection agent. Cells from these suspensions are also plated on solidified SH-30 medium containing an appropriate selection agent and incubated at about 25° C. in the dark Calli grown from the plated cells are subcultured every two weeks onto fresh medium. The cells which grow in the presence of the selection marker are presumed to be transformants.

B. Section is carried out as described except that the protoplast-derived cell colonies growing in the presence of the selection marker containing medium are placed on agar plates of SH-30 medium containing the selection marker and incubated at about 25° C. in the dark.

EXAMPLE 35

Regeneration of Transformed *Dactylis glomerata* L. Plants

A. *Dactylis glomerata* L. callus (obtained as described) derived from protoplasts is grown on solidified SH-30 medium, and subcultured every two weeks. Any embryos which form are removed and plated on germination medium (SH-O) and placed in the light (3800 to 4600 lx). Germination of these embryos occurs in 1 to 4 weeks and the resultant plantlets are placed on SH-O medium in the light to form root systems. They are moved into the greenhouse at the six to twelve leaf stage, and hardened off gradually.

B. Callus (obtained as described) derived from protoplasts is grown on SH-O medium solidified with 0.24% Gelrite in the light (3800 to 4600 lx), and subcultured every two weeks. The resultant plantlets are placed on a 1:1 mixture of SH-O and OMS media solidified with a combination of 0.12% Gelrite and 0.4% agar in the light to form root systems. They are moved to the greenhouse at the six to twelve leaf stage, and hardened off gradually.

C. Small plantlets are obtained as described in Examples 35A and 35B, and are placed on OMS medium solidified with 0.8% agar in the light to form root systems. They are moved to the greenhouse at the six to twelve leaf stage, and hardened off gradually.

D. Small plantlets are obtained as described in Example 35A above and are placed on a 1:1 mixture of SH-O and OMS media solidified with a combination of 0.12% GelRite and 0.4% agar in the light to form root systems. They are moved to the greenhouse at the six to twelve leaf stage, and hardened off gradually.

EXAMPLE 36

Production of Transgenic Wheat Plants
Cell Culture Maintenance

Callus cultures are maintained on 1 MS medium as described for example by "Murashige, T. and Skoog F., 1962, Physiol. Plant 15, 473–497" (MS salts, vitamins, iron, 3% sucrose, 0.7% agar, 1 mg/liter 2,4-D). The suitable callus cultures comprise among others Type II callus (a friable and embryogenic type of callus) obtained from "shoot-competent" cell cultures as described in "W. Wang and H. Nguyen, 1990, Plant Cell Reports 8 639–642") after recurrent subculture and visual selection. They are subcultured every two weeks and are kept in the dark at 26° C. Suspension cultures are maintained in 1 MS liquid medium and are subcultured twice weekly. They are kept in the dark at 26° C. and shaken at ≠125 rpm.

Cell Preparation for Bombardment

The cells are given a plasmolysis treatment before bombardment. Packed cell volume is measured and cells are diluted in 1 MS liquid medium with added osmoticum: 0.4M sorbitol for suspension cells and 0.6M sorbitol for callus cells. Cells are diluted such that the final packed cell volume per target is 1/20 ml for a fine suspension and 1/10 ml for callus. Diluted cells are placed in a 250 ml flask containing a stir bar and are stirred for a minimum of 30 minutes, up to a few hours. To plate the cells, 2 ml is withdrawn from the flask and pipetted into the top of a vacuum flask onto which a Whatman 2.5 cm GFA filter has been placed. The vacuum is applied until the cells are dried onto the filter, the filters are placed on 60×15 mm petri plates containing 5 ml of solid post bombardment plasmolysis medium: 1 MS containing 0.2M sorbitol for suspension cells, or 0.4M sorbitol for callus cells. Two filters are plated on each dish.

Particle Preparation

Gold particles (1.0 micron; from Bio-Rad) are washed by aliquoting into a microfuge tube, adding ≠1 ml 100% ethanol, vortexing, spinning down, removing the supernatant, and repeating twice with sterile water. After the final wash, as much water is removed as possible and polylysine solution (0.02% polylysine+15 mM ammonium acetate) is added to completely immerse the particles. The particles are vortexed, spun, and the supernatant removed. The particles are allowed to dry overnight in a laminar flow hood or for 30 minutes under a gentle nitrogen stream.

For a "full" particle preparation, weigh out 10 mg particles and place in sterile microfuge tube containing a stir bar. Add 100 ml (1 mg/ml) DNA (according to step I), vortex, add 10 ml 100 mM $Na_2HPO_4$, vortex, add 10 ml 100 mM $CaCl_2$, vortex, add 380 ml 100% ethanol, vortex. Stir suspension vigorously on stir plate while pipetting 3 ml onto each plastic flier (projectile). Allow particles to dry onto fliers for at least 15 minutes before bombarding.

Bombarding Cell Cultures

Bombarding of cell cultures is carried out using a device as described in EP-A . . . Invert the petri plate containing the cell filters onto the platform on top of the stage, centered over the particle flight opening. Place the clear lid over the top of the platform. Place a microprojectile onto the breech pin and close the breech. Push the "arm" button to fill the reservoir with the appropriate amount of helium gas (usually 1800–1900 psi). Pull the vacuum on the chamber to ≠27 mm. Turn off the vacuum, and push the "arm" and "fire buttons. Move the "arm" button on the "off" position. Each filter is usually shot twice.

Post bombardment Culture and Section

After bombardment the cells are kept in the dark overnight. The next day, filters are removed from plasmolysis medium and placed on 1 MS medium. Selection is applied 7–10 days post-bombardment for suspension cells and after 14 days for callus cells. Cells are scraped off the filters and spread onto the surface of plates containing 1 MS plus an appropriate selection agent, dependent on the selection marker gene used in plant transformation. Plates are incubated in the dark for several weeks. Resistant colonies that arise after a few weeks are transferred to IMS+selection agent Coloni that continue to proliferate for about 3–4 weeks are then transferred to "0.5 MS" maintenance medium: MS salts, vitamins, iron, 3% sucrose, 0.7% agar, 0.5 mg/liter 2,4-D. Tissue is subcultured onto this medium biweekly until embryogenic structures or tissue seems suitable for regeneration.

Regeneration

Tissue is transferred to MS medium containing either 3 mg/liter BAP or 1 mg/liter NAA+5 mg/liter GA, and plates are moved to the light. After 2–4 weeks, tissue is transferred to MS medium without hormones. Shoots that appear are placed in Magenta boxes containing either MS medium without hormones or MS medium with 0.5 mg/liter NAA. When sufficient root and shoot growth has occurred, plantlets are transferred to soil and placed in a phytotron.

EXAMPLE 37

GA 20-oxidase DNA from *Arabidopsis thaliana*

(a) Isolation of genomic DNA from *Arabidoposis thaliana*.

Seeds of *Arabidopsis thaliana* Landsberg erecta are surface sterilised by treatment with 5% sodium hypochlorite solution in 0.01% Tween-20 (Sigma), washed twice with water and suspended in 0.15% agar. The seeds are sown onto 0.8% agar containing Murashige and Skoog Medium supplemented with B5 vitamins (Sigma) and 5% sucrose in sterile Magenta containers (Sigma). Plants are grown for 4 weeks at 20° C. and shoot material is frozen in liquid nitrogen and stored at −70° C. Genomic DNA is isolated essentially as described by Murray and Thompson (Murray, M. G. and Thompson, W. F. (1980)). The frozen tissue, 10 g, is ground to a slurry in an ice-cooled mortar with a small amount of acid-washed sand. The homogenate is transferred to a polypropylene centrifuge tube and an equal volume of 2% (w/v) CTAB (cetyltrimethylammonium bromide, Sigma), 1.4M NaCl, 0.1M Tris-Cl pH 8.0, 20 mM EDTA added. After gentle mixing, the tube is incubated at 67° C. for 20 min with occasional mixing. The tube is removed from the water bath and 0.5 volumes of chloroform added, mixed gently and left at room temperature (20° C.) for 20 min with occasional inversion. The tube is centrifuged at 2000 g for 5 min at room temperature, the upper phase removed to a new tube and the lower phase discarded. To the upper phase is added 0.1 vol of 10% (w/v) CTAB, 0.7M NaCl and the chloroform extraction above is repeated. The upper phase is again decanted to a new tube and 2 volumes of 1% (w/v) CTAB, 50 mM Tris-Cl, pH 8.0, 10 mM EDTA added. This is mixed gently and left at room temperature for 1 hour, then centrifuged at 5000 g for 5 min. The pellet is dissolved in 50% (w/w) CsCl in TE buffer with ethidium bromide at 0.5 mg/ml. The solution is transferred to a Quick-seal tube (Beckman) and centrifuged in a vertical rotor (Beckman VTi90) for 16 hours at 80,000 rpm at 20° C. The DNA is visualised under natural light and removed with the aid of a syringe and needle. Ethidium bromide is removed by extraction four times with 5 volumes of butan-1-ol, previously equilibrated against NaCl-saturated water. The solution is diluted by the addition of 3 volumes of TE buffer (10 mM Tris-Cl pH 8.0, 1 mM EDTA) and DNA precipitated with 2 volumes of EtOH. The DNA is pelleted by centrifugation at 10,000 g for 10 min at 0° C., washed with 70% EtOH, dried in vacuo, and dissolved in TE buffer. The DNA concentration is determined by its absorbance at 260 nm.

(b) Construction of a cDNA library.

Seeds of *Arabidopsis thaliana* gal are induced to germinate by overnight incubation in a 10 mM solution of $GA_3$, shaking at room temperature. The seeds are washed twice with water, suspended in 0.15% agar in water and sown directly onto seed compost. Plants are grown for 5 weeks and shoot tissue harvested directly into liquid nitrogen and stored at −70° C. Poly A⁺ RNA is isolated as described by Bartels and Thompson (1983). Double stranded cDNA is produced from 5 mg mRNA using an oligo-dT primer with the cDNA Synthesis Plus Kit (Amersham) and EcoRI adapters added using the λgt11 Cloning Kit (Amersham). The cDNA is ligated into EcoRI-cut, dephosphorylated λZapII arms (Stratagene) and packaged using Gigapack Gold (Strategene). A primary library of 320,000 recombinants is produced, and half of this is amplified by passage through $E.$ $coli$ XL1-Blue (Stratagene) as described by the manufacturer.

(c) Plating the cDNA library for screening.

A 50 ml aliquot of 2xYT (1.6% Bactotryptone, 1% yeast extract, 0.5% NaCl) including 0.2% maltose and 10 mM $MgSO_4$ is inoculated with a single colony of $E.$ $coli$ XL1-Blue. This is grown overnight at 30 C., transferred to a sterile centrifuge tube and spun down at 2000xg for 5 min, room temperature. The cells are resuspended in 10 mM $MgSO_4$. In sterile 15 ml tubes, 500 ml $E.$ $coli$ cells is mixed with 50,000 recombinant bacteriophage from the amplified library and incubated at at room temperature for 10 min followed by 37 C. for 15 min. Molten top agarose (0.75% in 2xYT/0.2% maltose/10 mM $MgSO_4$), 6.5 ml, is added at 48 C. and the tube contents quickly poured onto a prewarmed 10 cm×10 cm plate of 1.5% agar in 2xYT/0.2% maltose/10 mM $MgSO_4$. The plates are incubated inverted at 37 C. for 6 hours and then stored overnight at 4° C. Duplicate nitrocellulose filters are labelled and placed onto the agar plates for 1 min each. The filters are air dried and treated for 5 min each in 1.5M NaCl, 0.5M NaOH (denaturation); 3M NaCl, 1M Tris-Cl pH 6.5 (neutralization); 0.6M NaCl, 60 mM trisodium citrate (fixation). The filters are again air dried on filter paper and baked in vacuo, between layers of filter paper, at 80 C for 2 hrs.

(d) Preparation of labelled probe.

The insert from clone pAt2204, consisting of a PCR fragment from Arabidopsis genomic DNA, is labelled with $P^{32}$ by primer extension. Plasmid DNA, 2 mg in 20 mg TE buffer, is denatured by the addition of 5 ml of 1M NaOH, incubated at room temperature for 5 min and neutralized by spin-desalting through a 0.5 ml column of Sepharose CL-6B in TE, spun at 2,000 rpm for 2.5 min. To 10 ml of this denatured DNA is added 2 ml universal sequencing primer (New England Biolabs) and 2 ml 100 mM Tris-Cl pH 8.0, 50 mM $MgCl_2$. This is incubated at 37° C. for 15 min and 4 ml $^{32}$P-dCTP (10 mCi/ml; 3,000 Ci/mmol; Amersham), 1 ml dGAT mix (0.2 mM each dGTP, dATP, dTTP), 1 ml Klenow DNA polymerase (1 u/ml; Gibco-BRL) are added. After 15 min at room temperature (20° C.), 1 ml of 2 mM dCTP is added; after a further 5 min at room temperature, 2.2 ml of 10× HindIII buffer (Gibco-BRL) and 10 units of HindIII are added and the tube incubated at 37° C. for 45 min. To terminate the reaction, 8 ml of formamide dye loading mix (Pharmacia) is added and the DNA is denatured by heating to 95° C. for 2 min. The products are loaded onto a 1.5 cm well on a 1 mm thick, 20 cm×20 cm polyacrylamide gel (6% (w/v) polyacrylamide (acrylamide:methylenebisacrylamide=39:1), 1×TBE (90 mM Tris, 90 mM Boric acid, 2.5 mM EDTA), 8M urea). The gel is run at 25 W constant power for 1 hour, and one glass plate is removed and the gel covered with cling-film. The position of the labelled band is identified by autoradiography against Kodak X-OMAT LS for 5 min. The labelled band is excised from the gel and placed into a dialysis bag, 1 cm wide, with 0.4 ml TE buffer. This is sealed at each end with a dialysis clip and placed in a horizontal electrophoresis tank filled with TBE buffer. The labelled DNA is eluted at 100 v for 30 min and recovered from the dialysis bag in the TE buffer.

(e) Hybridization.

Nitrocellulose filter lifts prepared as, above are wetted in water and prehybridized for 2 hours at 42° C. in hybridization buffer (50% formamide, 50 mM NaPi pH 6.3, 0.75M NaCl, 75 mM trisodium citrate, 0.1% (w/v) bovine serum albumin, 0.1% (w/v) Ficoll 400, 0.1% (w/v) polyvinylpyrrolidone, 0.1% (w/v) sodium dodecyl sulphate (SDS), 100 mg/ml sonicated calf thymus DNA). The probe is boiled for 2 min, mixed with 25 ml of hybridization buffer and sealed into a polythene bag with the prehybridized filters. Hybridization is carried out at 42° C. overnight, and unbound probe is removed by washing in 0.3M NaCl, 30 mM trisodium citrate, 0.1% (w/v) SDS at room temperature for 15 min, and in 15 mM NaCl, 1.5 mM trisodium citrate, 0.1% SDS at 60° C. for 10 min. Positively-hybridizing plaques are identified by autoradiography against Kodak X-OMAT AR film with intensifying screens, overnight at −70° C.

Positive plaques are isolated in pure form by plating the primary positives and probing lifts with the labelled insert of pAt2204 as described above. Pure recombinant λZapII clones are rescued into pBluescript (Stratagene) as described by the manufacturer.

(f) DNA seguencing.

The DNA sequence of the inserts of the primary cloned PCR fragments are obtained with the T4 Polymerase Sequencing Kit (Pharmacia). The insert of the full-length clone pAt2301 is sequenced by the construction of a nested set of transpose insertion clones, using the TN1000 Nested Set Kit (Gold Biotechnology, St. Louis, Mo.) followed by sequencing of individual clones with the T4 Polymrase Sequencing Kit (Pharmacia).

EXAMPLE 38

Isolation and Characterisation of DNA Clone pAt2301 and pAt2353, Encoding a Gibberellin 20-oxidase From *Arabidopsis thaliana*

(a) PCR amplification and cloning of internal fragments of 20-oxidase-related genes from Arabidopsis genomic DNA. Degenerate, oligodeoxynucleotide primers are designed based on amino acid regions conserved between the *Cucurbita maxima* cotyledon gibberellin 20-oxidase and other plant dioxygenases, including the tomato E8 ripening-related protein, tomato ethylene-froming enzyme, hyoscamine 6-hydroxylase from *Hyoscyamus niger*, barley flavanone 3-hydroxylase and the A2 gene from maize. The upstream and downstream primers contained restriction endonuclease cleavage sites for HindIII and EcoRI, respectively, at their 5' termini.

Upstream primer

```
Amino Acid:      Asn    Tyr    Tyr    Pro Thr Cys
DNA         5'-GCAAGCTT-AA(CT)-TA(TC)-TA(TC)-CCX-ACX-TG-3' (SEQ ID NO:10)
```

Downstream primer

```
Amino Acid:   Phe   Val   Ile   Asn   Ile   Gly  Asp

DNA:       3'-AA(GA)-CAX-TA(AGT)-TT(GA)-TA(AGT)-CCX-CT-TAAGCG-5'   (SEQ ID NO:11)
```

PCR reactions contained 50 ng genomic DNA from *Arabidopsis thaliana* strain Landsberg erecta (Redei, GP (1962)), 2.5 µg each degenerate primer, 25 µM each dNTP and 1 unit of AmpliTaq (Perkin Elmer Cetus) in a total volume of 25 µl AmpliTaq buffer containing 1.5 mM $MgCl_2$, and overlayed with 25 µl mineral oil. Reactions are incubated at 94° C. for 5 mins followed by 40 cycles of 94° C. 1 min, 35° C. 2 min, 72° C. 3 min. The 72° C. step is increased by 5 sec each cycle. The reactions are then incubated at 72° C. for 10 minutes.

The products of PCR amplification are separated by electrophoresis through a 1.5% agarose gel in Tris-Borate-EDTA buffer (90 mM Tris, 90 mM Boric acid, 2.5 mM EDTA). A faint band of approx 190 bp is identified and eluted from the gel into 100 µl of TE buffer (10 mM Tris-Cl pH 8.0, 1 mM EDTA), 1 µl of which is used as substrate in a PCR reaction under the conditions described above. The products are again separated by agarose gel electrophoresis and the 190 bp amplified band purified from the agarose. This is digested with EcoRI and HindIII and one tenth of the products ligated to 100 ng of pUC19 (Pharmacia), previously digested with EcoRI and HindIII and dephosphorylated. The products of the ligation reaction are introduced into *E. coli* strain XL1-Blue (Statagene) by transformation and grown on 2xYT agar plates containing 100 µg/ml ampicillin. Plasmid DNA is isolated from single colonies, and sequenced by the dideoxynucleotide chain termination method.

One of these clones, pAt2204, contained an insert whose predicted amino acid sequence is 67% identical to that of pumpkin gibberellin 20-oxidase:

```
AATTACTACCCTACGTGTATAAAACCAGATCTCACACTAGGAACAGGACCTCATTGTGAT

AsnTyrTyrProThrCysIleLysProAspLeuThrLeuGlyThrGlyProHisCysAsp

CCAACATCTCTTACCATCCTTCACCAAGACCATGTTAATGGCCTTCAAGTCTTTGTGGAA

ProThrSerLeuThrIleLeuHisGlnAspHisValAsnGlyLeuGlnValPheValGlu

AATCAATGGCGCTCCATTCGTCCCAACCCCAAGGCCTTTGTAATTAACATCGGA        (SEQ ID NO:12)

AsnGlnTrpArgSerIleArgProAsnProLysAlaPheValIleAsnIleGly        (SEQ ID NO:13)
```

(b) Isolation of a full-length cDNA clone corresponding to PCR clone pAt2204.

The insert of pAt2204 is labelled with 32p-dCTP and used to probe nitrocellulose filter lifts of a full-length cDNA library, constructed in λZapII (Stratagene) from poly-$A^4$ RNA isolated from shoot material of the gibberellin-deficient gal mutant of *Arabidopsis thaliana* (Koornneef M. and van der Veen, J. H. (1980)). The hybridisation is carried out in 50% fromamide, 50 mM sodium phosphate pH 63, 0.75M NaCl, 75 mM sodium citrate, 0.1% bovine serum albumin, 0.1% Ficoll 400, 0.1% polyvinylpyrrolidone 360, 0.1% sodium dodecyl sulphate and 100 µg/ml salmon testes DNA at 42° C. overnight. Filters are washed in 15 mM NaCl, 1.5 mM sodium citrate at 42° C. for 10 min. Hybridising plaques are identified by autoradiography and purified by successive rounds of hybridisation. Positive clones are converted into pBluescript clones by plasmid rescue and characterised by EcoRI digestion and DNA sequencing.

Clone pAt2353 and clone pAt2301, containing a 1.3 kbp insert, are chosen for heterologous expression studies.

(c) Expression of cDNA clone pAt2301 in *E. coli*

The 1.3 kbp insert of pAt2301 is excised with EcoRI, purified by agarose gel electrophoresis and ligated to expression vector pTrcHisA (Invitrogen), previously cut with EcoRI and dephosphorylated. Ligation products are introduced into *E. coli* strain TOP10 (Invitrogen) by transformation and selected by growth on 2xYT agar with ampicillin at 100 µg/ml. Plasmid DNA is isolated from a number of the resulting clones and the orientation of the cDNA insert determined by HindIII digestion. Clone pAt2328 contained a cDNA insert in sense orientation, and is used to inoculate 50ml of 2xYT containing carbenicillin at 100 µg/ml. After 2 hrs growth shaking at 37° C., IPTG (Isopropyl-b-D-thiogalactopyranoside) is added to 1 mM and the cultures are grown for a further 5 hrs. The cells are collected by centrifugation and suspended in 4 ml of 100 mM Tris-Cl pH 7.5, 4 mM DTT and sonicated on ice for a total of 90 secs. The samples are then frozen in liquid nitrogen, thawed by hand and insoluble material removed by centrifugation at 15,000xq for 5 min. The resulting supernatant material is stored at −80° C. and subsequently used for enzyme assay.

The supernatant (90 µl) is incubated with $[^{14}C]GA_{12}$ (10,000 dpm) and dioxygenase co-factors as given in Example 1 in 100 µl total volume at 30° C. for 5 hr. Separation of products by HPLC showed production of $[^{14}C]GA_{15}$, the identity of which is confirms by combined gas chromatography-mass spectrometry (GC-MS).

EXAMPLE 39

Isolation of cDNA Clone YAP169, Encoding a Gibberellin 20-oxidase From *Arabidopsis thaliana*

A TBLASTN program is ran on the DBEST (database of expressed sequence tags) held at the NIH (BLAST@NCBI.NLM.NIH.GOV) using the full amino acid sequence of the Arbabidopsis cDNA clone At2301 to search for related sequences. The search program translates the DNA sequences in the database into amino acid sequences in both orientations and all three reading frames. The DBEST database contains partial sequences for cDNAs obtained at random as part of the systematic Arbabidopsis cDNA sequencing program. The method for producing Arbabidopsis sequences has been published by Hofte et al (1993).

Running the TBIASTIN program an additional clone (YAP169) can be identified that owing to its sequence homology to clone pAt2301 is likely to encode a dioxygenase. Expressing the cDNA in *E. coli* as described previously confirms that the expressed protein has 20-oxidase activity. Clone YAP169 was kindly provided by M. Delseny of the University of Perpignan, France.

EXAMPLE 40

Transformation of *Arabidopsis thaliana*

(a) Construction of a PR1-tml vector.

Construction of a vector in which the double CaMV 35S promoter in pCGN1761 is replaced by the chemically-inducible promoter from the Arabidopsis PR1a gene. The oligonucleotide 5'-GAGAATTCTAAGTIGATAATGGTTATTG-3' (SEQ ID NO: 14) is used in conjunction with the M13 universal sequencing primer in a PCR reaction, using plasmid pATPR1-P as substrate. The product of this reaction, a 4.2 kbp fragment containing the PR1 promoter, is digested with EcoRI and HindIII. Plasmid pCGN1761 is digested with EcoRI and HindIII to remove the double 35S promoter and the resulting 5 kbp vector fragment is ligated with the PR1 promoter fragment. The ligation products are introduced into *E. coli* by transformation and a colony containing the PRI promoter identified. This plasmid is named pPR1-tml.

(b) Construction of 35S-20oxidase (Arabidopsis)chimaeric genes (the three Arabidopsis) 20-oxidase cDNAs each cloned into pCGN1761)

The three GA 20-oxidase cDNAs (At2301, At2353 and YAP169) are each expressed in sense and antisense orientation behind the constitutive CaMV 35S promoter, by PCR amplification of each open reading frame and transfer into the vector pCGN1761. An oligonucleotide is synthesized corresponding to the translation initiation codon and the succeeding 12–13 bases of the coding strand of each cDNA, and incorporating an EcoRI site at the 5' ends: for pAT2301 the oligonucleotide is 5'-GAGAATTCAAAATGGCCGTAAGTTTCG-3' (SEQ ID NO: 15); for pAt2353 the oligonucleotide is 5'-GAGAATTCAGAAATGGCGATACTATGC-3' (SEQ ID NO: 16); for YAP169 the oligonucleotide is 5'-GAGAATTCAAAAATGGCAACGGAATGC-3' (SEQ ID NO: 17). Each of these oligonucleotides is used in conjunction with the M13 universal sequencing primer in PCR reactions, using the appropriate plasmid substrate (pAt2301, pAT2353 and YAP169 respectively). The PCR products from each reaction are digested with EcoRI and cloned into the EcoRI site of pCGN1761 using standard techniques. Colonies carrying each of the three cDNA inserts in sense and antisense orientations relative to the 35S promoter are recovered and are named pCGN1761-35S-At2301-sense, pCGN1761-35S-At2301-antisense, pCGN1761-35S-At2353-sense, pCGN1761-35S-At2353-antisense, pCGN1761-35S-YAP169-sense and pCGN1761-35S-YAP169-antisense respectively.

(c) Construction of PR1-20-oxidase (Arabidopsis) chimaeric genes (the three Arabidopsis 20-oxidase cDNAs each cloned int pPR1-tml.

The EcoRI-digested PCR products derived from pAt2301, pAt2353 and YAP169, described above, are cloned into the EcoRI site of pPR1-tml, to yield each Arabidopsis GA 20-oxidase cDNA in sense and antisense orientation with respect to the chemically-inducible PR1 promoter. The constructs are named pPR1-At2301-sense, pPR1-At2301-antisense, pPR1-At2353-sense, pPR1-At2353-antisense, pPR1-YAP169-sense and pPR1-YAP169-antisense.

(d) Transfer of the 35S-20-oxidase (Arabidopsis) fusions from pCGN1761-35S-At2301-sense, pCGN1761-35S-At2301-antisense, pCGN1761-35S-At2353-sense, pCGN1761-35S-At2353-antisense, pCGN1761-35S-YAP169-sense and pCGN1761-35S-YAP169-antisense to the binary vector PCIB200.

The 35S-20-oxidase expression cassettes are excised from constructs pCGN1761-35S-At2301-sense, pCGN1761-35S-At2301-antisense, pCGN1761-35S-At2353-sense, pCGN1761-35S-At2353-antisense, pCGN1761-35S-YAP169-sense and pCGN1761-35S-YAP169-antisense by digestion or partial digestion with XbaI. Each of these cassettes is cloned into the XbaI site of pCIB200 [see Example 11] generating binary vectors capable of expressing the cDNA inserts of pAt2301, pAt2353 and YAP169 in sense and antisense orientation behind the double 35S promoter.

(e) Transfer of the PR1-20-oxidase (Arabidopsis) fusions from pPR1-At2301-sense, pPR1-At2301-antisense, pPR1-At2353-sense, pPR1-At2353-antisense, pPR1-YAP169-sense and pPR1-YAP169-antisense to the binary vector pCIB200.

The PR1-20-oxidase expression cassettes are excised from constructs pPR1-At2301-sense, pPR1-At2301-antisense, pPR1-At2353-sense, pPR1-At2353-antisense, pPR1-YAP169-sense and pPR1-YAP169-antisense by digestion or partial digestion with XbaI. Each of these cassettes is cloned into the XbaI site of pCIB200 generating binary vectors capable of expressing the cDNA inserts of pAt2301, pAt2353 and YAP169 in sense and antisense orientation behind the chemically-inducible PR1 promoter.

(f) Transformation of *Arabidopsis thaliana*.

The above constructs will be introduced into *Arabidopsis thaliana* by *Agrobacterium tumifaciens*-mediated transformation as described in Example 12 and 13.

BIBLIOGRAPHY

Bartels and Thompson R. D. (1983) Nucleic Acids Res. 111:2961–2977
Bevan et al, Nature 304: 184–187 (1983)
Benfey et al, EMBO 9: 1677–1684 (1990)
Christou et al, Plant Physiol 87: 671–674 (1988)
Comellison et al, EMBO 5: 37–40 (1986)
Crossway et al, BioTechniques 4: 320–334 (1986)
Datta et al, Bio/Technology 8: 736–740 (1990)
Della-Cioppa et al, Plant Physiology 84: 965–968 (1987)
Elzen et al, Plant Molecular Biology 5: 299–392 (1985)
Erlich, (ed.), PCR Technology, Stockton Press, New York (1989)
Facciotti et al, Bio/Technology 3: 241–246 (1985)
Fromm et al, Bio/Technology 8: 833–839 (1990)
Goff StA et al, EMBO J 9:2517–2522 (1990)
Gordon-Kamm et al, Plant Cell 2: 603–618 (1990)
Gray, D. J. and Conger et al, Plant Tissue Organ Cult 4: 123–133 (1985)
Grimsley et al, EP-A-0 267 159
Hanning, G. E. and Conger et al, Theor. Appl. Genet. 63: 155–159 (1982)
Haymes B. T. et al, Nucleic Acid Hybridisation: a Practical Approach, IRL Press, Oxford, England (1985)
Heijne et al, Eur J Biochem, 180: 535–545 (1989)
Hinchee et al, Biotechnology 6: 915–921 (1988)
Höfte et al, The Plant Journal 4: 1051–1061 (1993)
Horsch et al, Science 227: 1229 (1985)
Huang et al, Proc Nat Acad Sci USA, 88: 10716–10720 (1991)

Jefferson, Plant Molecular Biology Reporter 5: 387–405 (1987)
Klein et al, Proc Nat Acad Sci USA 85: 4305–4309 (1988)
Klein et al, Bio/Technology 6: 559–563 (1988)
Klein et al, Plant Physiol. 91: 440–444 (1989)
Koornneef M. and van der Veen J. H. (1980) Theor. Appl. Genet. 58:257–263
Koziel M. G. et al, Bio/Technology 11: 194–200 (1993)
McBride et al, Plant Molecular Biology 14: 266–276 (1990)
Maniatis et al, Molecular Cloning: A Laboratory Manual, Cold Spring Harbor Laboratory,
Cold Spring Harbor, New York (1982)
Matsuoka K. and Nakamura K., Proc Natl Acad Sci USA, 88: 834–838 (1991)
Maxam and Gilbert, Proc Nat Acad Sci USA 74: 560–564 (1977)
McCabe et al, Bio/Technology 6: 923–926 (1988)
Messing et al, Gene 19: 259–268, 1982
Mohnen et al, EMBO J., 4: 1631–1635 (1985)
Morelli et al, Nature 315: 200–204 (1985)
Mullis et al, Meth. Enzymol. 155: 335–350 (1987)
Murashige T. and Skoog F., Physiologia Plantarum 15: 473 (1962)
Murray M. G. and Thompson W. F. (1980) Nucleic Acids Res. 8:4321–4325
Negrutiu et al, Mol Gen Genet 199: 330–337 (1985)
Neuhaus et al, Theor Appl Genet 75, 30–36 (1987)
Paszkowski et al, EMBO J. 3: 2717–2722 (1984)
Petit et al, Mol Gen Genet 202: 388 (1986)
Pierce et al, Plant Gene Systems and their Biology, (Alan R. Liss, Inc.) pp. 301–310
Redei, G. P. (1962) Single locus heterosis. Z. Vererbungsl. 93:164–170
Riggs et al, Proc Nat Acad Sci USA 83: 5602–5606 (1986)
Rothstein et al, Gene 53: 153–161 (1987)
Sambrook J. et al, Molecular Cloning, A Laboratory Manual, Second Ed, Cold Spring Harbor Laboratory Press, 1989
Sanford et al, U.S. Pat. No. 4,945,050
Sanford et al, Particulate Science and Technology 5:27–37 (1987)
Sanger, Proc Nat Acad Sci USA 74:5463–5467 (1977)
Schekman, TIBS, 188, 1985
Schmidhauser et al, J Bacteriol 164: 446455, 1985
Schmitz et al, Plant Cell, 1: 783–791, 1989
Schocher R. J. et al, Bio/Technology, 4: 1093–1096 (1986)
Shillito et al, Bio Technology, 3, 1099–1103 (1985)
Southern, J. Mol. Biol. 98: 503 (1975)
Thompson et al, EMBO J 6: 2519–2523 (1987)
Velten et al, EMBO J. 3:2723–2730 (1984)
Wang and Nguyen, Plant Cell Reports 8: 639–642, 1990
Wang Y-C et al, Plant Mol. Biol. 11: 433439 (1988)
Weissing et al, Annual Rev. Genet. 22: 421477 (1988)

Patent Literature

EP-A 0 267 159 WO 89/07647
EP-A 0 306 139 U.S. Pat. No. 4,945,050
EP-A 0 332 104
EP-A 0 434 616
EP-A 0 462 065
EP-A 0 478 502

What is claimed is:

1. An isolated DNA sequence comprising (a) a DNA sequence which encodes a polypeptide exhibiting GA 20-oxidase activity having the amino acid sequence according to SEQ ID NO. 2, 4 or 6 or (b) a DNA sequence which hybridizes with the DNA sequence of (a) or its complement under hybridizing conditions and encodes a polypeptide exhibiting GA 20-oxidase activity.

2. The DNA sequence according to claim 1, wherein the polypeptide acts on one or more substrates selected from the group consisting of $GA_{12}$, $GA_{53}$, $GA_{15}$ (open or closed lactone), $GA_{44}$ (open or closed lactone), $GA_{24}$, $GA_{19}$ and $GA_{23}$.

3. The DNA sequence according to claim 1, wherein the sequence is a cDNA clone.

4. The DNA sequence according to claim 1, wherein the sequence encodes a GA 20-oxidase obtained from monocotyledonous or dicotyledonous plants or fungi.

5. The DNA sequence according to claim 4, wherein the sequence encodes a GA 20-oxidase obtained from *Cucurbita maxima*.

6. The DNA sequence according to claim 4, wherein the sequence encodes a GA 20-oxidase obtained from *Arabidopsis thaliana*.

7. A purified DNA encoding a polypeptide exhibiting GA 20-oxidase activity having the sequence set forth in SEQ ID NO 1.

8. A purified DNA encoding a polypeptide exhibiting GA 20-oxidase activity having the sequence set forth in SEQ ID NO 3.

9. A purified DNA encoding a polypeptide exhibiting GA 20-oxidase activity having the sequence set forth in SEQ ID NO 5.

10. A method of preparing a DNA sequence according to claim 1, comprising preparing a cDNA library from a source organism, hybridizing the library with a DNA sequence which encodes the amino acid sequence according to SEQ ID NO: 2, 4 or 6, and isolating the DNA sequence.

11. A recombinant DNA comprising the DNA sequence according to any one of claims 1–9.

12. A method of preparing a polypeptide exhibiting GA 20-oxidase activity, which comprises expressing in a host organism the DNA sequence as claimed in any one of claims 1–9, and isolating the expressed polypeptide.

13. The method according to claim 12, in which said expression takes place in a transformed host cell.

14. A transformed host cell comprising the recombinant DNA of claim 11 wherein the recombinant DNA comprises the DNA sequence encoding the polypeptide exhibiting GA 20-oxidase activity in operable linkage with an expression signal including promoter and termination sequences which causes expression of said DNA in the host cell.

15. A chimaeric gene construct comprising the recombinant DNA of claim 11 wherein the recombinant DNA comprises the DNA sequence encoding the polypeptide exhibiting GA 20-oxidase activity in operable linkage with a plant expression signal including promoter and termination sequences causing the gene to express a polypeptide exhibiting GA 20-oxidase activity within a plant.

16. A chimaeric gene construct comprising at least a part of the DNA sequence of claim 1 in reverse order, in operable linkage with plant expression signals including promoter and termination sequences causing the reverse DNA sequence to express antisense mRNA within a plant.

17. The chimaeric gene construct according to claim 15, wherein the promoter is an inducible promoter.

18. The chimaeric gene construct according to claim 15, wherein the promoter is a tissue-preferential or tissue-specific promoter.

19. The chimaeric gene construct according to claim 18, wherein the tissue-preferential or tissue-specific promoter is a pith-specific promoter.

20. The chimaeric gene construct according to claim 17, wherein the promoter is inducible by a chemical.

21. The chimaeric gene construct according to claim 20, wherein the promoter has a sequence of an Arabidopsis PR1a gene promoter.

22. A method of identifying a DNA sequence comprising a DNA region encoding a polypeptide exhibiting GA 20-oxidase activity which comprises preparing a cDNA or a genomic library from a source organisms, screening the library by hybridisation using the DNA according to any one of claims 1 and 7–9 as a hybridisation probe under hybridizing conditions, and identifying a DNA sequence which hybridize to the DNA and encodes a polypeptide which exhibit GA 20-oxidase activity.

23. A DNA sequence comprising a DNA region encoding a polypeptide exhibiting GA 20-oxidase activity identified by the method according to claim 22.

24. A method of preparing a polypeptide exhibiting GA 20-oxidase activity, which comprises expressing in a host organism the DNA sequence of claim 11, and isolating the expressed polypeptide.

25. The chimaeric gene construct according to claim 16, wherein the promoter is an inducible promoter.

26. The chimaeric gene construct according to claim 16, wherein the promoter is a tissue-preferential or tissue-specific promoter.

27. The chimaeric gene construct according to claim 26, wherein the tissue-preferential or tissue-specific promoter is a pith-specific promoter.

28. The chimaeric gene construct according to claim 25, wherein the promoter is inducible by a chemical.

29. The chimaeric gene construct according to claim 28, wherein the promoter has a sequence of an Arabidopsis PR1a gene promoter.

30. The DNA sequence according to claim 1, wherein the DNA sequence hybridizes with the DNA sequence of (a) by prehybridizing for 2 hours at 42° C. in a hybridization buffer of 50% formamide, 50 mM NaPi pH 6.3, 0.75M NaCl, 75 mM trisodium citrate, 0.1% (w/v) bovine serum albumin, 0.1% (w/v) Ficoll 400, 0.1% (w/v) polyvinylpyrrolidone, 0.1% (w/v) sodium dodecyl sulphate (SDS), 100 mg/ml sonicated calf thymus DNA, hybridizing in the hybridization buffer overnight at 42° C. and washing in 0.3M NaCl, 30 mM trisodium citrate, 0.1% (w/v) SDS at room temperature for 15 min. and in 15 mM NaCl, 1.5 mM trisodium citrate, 0.1% SDS at 60° C. for 10 min.

31. The method according to claim 22, wherein the hybridizing conditions comprises prehybridizing for 2 hours at 42° C. in a hybridization buffer of 50% formamide, 50 mM NaPi pH 6.3, 0.75M NaCl, 75 mM trisodium citrate, 0.1% (w/v) bovine serum albumin, 0.1% (w/v) Ficoll 400, 0.1% (w/v) polyvinylpyrrolidone, 0.1% (w/v) sodium dodecyl sulphate (SDS), 100 mg/ml sonicated calf thymus DNA, and hybridizing in the hybridization buffer overnight at 42° C. and washing in 0.3M NaCl, 30 mM trisodium citrate. 0.1% (w/v) SDS at room temperature for 15 min. and in 15 mM NaCl, 1.5 mM trisodium citrate. 0.1% SDS at 60° C. for 10 min.

32. A vector comprising the chimeric gene construct according to any one of claims 15–21, 25–29.

33. A host cell transformed with the chimeric gene construct according to any one of claims 15–21, 25–29.

34. The host cell according to claim 33, wherein the host cell is of bacterial or plant origin.

* * * * *

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 1395 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iii) ANTI-SENSE: NO (vi) ORIGINAL SOURCE:
      (A) ORGANISM: Cucurbita maxima (vii) IMMEDIATE SOURCE:
      (B) CLONE: Clone pB11

(xi) SEQUENCE DESCRIPTION: SEQ ID NO: 1:

```
CTTCTTTGCA TGCAATGGCT TTGAACGGCA AGGTGGCAAC CGAATCCGCT CCCTCAAACT      60

TGAATGAGGA GATGAAAGGG GAGTACCGTC CGCCATTTGG GGGCTCCGAC GAGTCAAAGG     120

TGCCGGAGGA TTTCATTTGG TCGGAAAAGT TTGAGGCATC CGAGTTGCTG CCGGTGCTGG     180

ATGTTCCAAC TATTGACTTG GAAAAGTTTA TGAGTGGCGA CAAAAGTTAT GTGGAAGAGG     240

CGACAAGGCT GGTGGATGAG GCTTGTAGAC AACATGGCAT ATTTTTTGTG GTGAACCATG     300
```

```
GAGTGGACAT AGAAATGATG GGCCGTGTTC ATGACTGTAT GAATGAGTTC TTTACAATGC        360

CTTTGGATGT GAAGCAGAGG GCTAAGAGGA AGGTAGGTGA GAGTTATGGA TATACCAATA        420

GCTTCTTTGG GAGATTCGCG TCCAATCTTC CATGGAAGGA AACCTTTTCC CTTCGCTGTG        480

TGGCTGCTCA AAACTCCTCC GCGGCTCATG ACTATGTTCT TGACACTTTA GGCCCATCAT        540

TCTCCCATCA TGGGAAGGCG TATCAAGAGT GTGGGATAGC ATTGAACGAG CTTGGTACGA        600

AGATTGTGGA GCTTTTGGGG CTTAGCCTTG GCATTTCAAG AGAATACTTC AAGAATTTCT        660

TCGAGGACAA CGATTCAATA TTGAGGCTTA ATTACTACCC AACATGCGAC AAGCCAGAGG        720

TTGTGTTGGG AACTGGCCCT CACACTGATC CCACCTCCGT CACAATCCTT CACCAAGACC        780

CTGTCAGTGG CCTTCAAGTG TGCTCCAATG ATCAATGGTA TTCAATTCCT CCAAACCCAG        840

AAGCCTTTGT CATCAACATC GGTGACACTT TCACGTCTCT CACGAATGGG ATTTACAAGG        900

GCTGCATACA CCGCGCTGTA GTGAATTCCA TGAATGCAAG AAAATCATTG GCCTTCTTTC        960

TGTGTCCATC GCATGACAAA GTGGTGAGAG CACCGGAGGA ATTGGTGGAG AAGAGTCCAC       1020

CACGAAAGTA TCCAGATTAT AAATGGCCAA TGTTGCTTGA AATGACCCAA AAGCGTTACC       1080

GACCTGATTG CAACACTTTG GAAGCCTTCA AAACTTGGGT TCAAGAGGGA AAGGCGTTGG       1140

ACACTGGGTC CACTATTACC GCCCCGTCTG CTTAAACCAA CCGTATCTAT GTCTCTCTAT       1200

GTATGCCAAT AAGTGTTTCT ACATTTACGA GCTTTCTAGG GAAGAAGAAC ATCGTGTAGG       1260

GTTCGGTCTA TGTCTGTCTT ATGTGTTGCT GGAAGTTGCA ATTAAAATAA ACCCTTTAAT       1320

ATCACATGTT CTTACTTTGC TCAAAAAAAA AAAAAAAAAA AAAAAAAAAA AAAAAAAAAA       1380

AAAAAAAAAA AAAAA                                                       1395

(2) INFORMATION FOR SEQ ID NO: 2:

(i) SEQUENCE CHARACTERISTICS:
        (A) LENGTH: 386 amino acids
        (B) TYPE: amino acid
        (C) STRANDEDNESS: single
        (D) TOPOLOGY: linear (ii) MOLECULE TYPE: protein (iii) HYPOTHETICAL: NO (iii) ANTI-SENSE: NO (v) FRAGMENT TYPE: internal (vi) ORIGINAL SOURCE:
         (A) ORGANISM: Cucurbita maxima (vii) IMMEDIATE SOURCE:
          (B) CLONE: Protein zu clone pB11

(xi) SEQUENCE DESCRIPTION: SEQ ID NO: 2:

Met Ala Leu Asn Gly Lys Val Ala Thr Glu Ser Ala Pro Ser Asn Leu
  1               5                  10                  15

Asn Glu Glu Met Lys Gly Glu Tyr Arg Pro Phe Gly Gly Ser Asp
             20                  25                  30

Glu Ser Lys Val Pro Glu Asp Phe Ile Trp Ser Glu Lys Phe Glu Ala
         35                  40                  45

Ser Glu Leu Leu Pro Val Leu Asp Val Pro Thr Ile Asp Leu Glu Lys
     50                  55                  60

Phe Met Ser Gly Asp Lys Ser Tyr Val Glu Glu Ala Thr Arg Leu Val
 65                  70                  75                  80

Asp Glu Ala Cys Arg Gln His Gly Ile Phe Phe Val Val Asn His Gly
```

```
                     85                  90                  95
Val Asp Ile Glu Met Met Gly Arg Val His Asp Cys Met Asn Glu Phe
                    100                 105                 110
Phe Thr Met Pro Leu Asp Val Lys Gln Arg Ala Lys Arg Lys Val Gly
            115                 120                 125
Glu Ser Tyr Gly Tyr Thr Asn Ser Phe Phe Gly Arg Phe Ala Ser Asn
        130                 135                 140
Leu Pro Trp Lys Glu Thr Phe Ser Leu Arg Cys Val Ala Ala Gln Asn
145                 150                 155                 160
Ser Ser Ala Ala His Asp Tyr Val Leu Asp Thr Leu Gly Pro Ser Phe
                165                 170                 175
Ser His His Gly Lys Ala Tyr Gln Glu Cys Gly Ile Ala Leu Asn Glu
            180                 185                 190
Leu Gly Thr Lys Ile Val Glu Leu Leu Gly Leu Ser Leu Gly Ile Ser
        195                 200                 205
Arg Glu Tyr Phe Lys Asn Phe Phe Glu Asp Asn Asp Ser Ile Leu Arg
        210                 215                 220
Leu Asn Tyr Tyr Pro Thr Cys Asp Lys Pro Glu Val Val Leu Gly Thr
225                 230                 235                 240
Gly Pro His Thr Asp Pro Thr Ser Val Thr Ile Leu His Gln Asp Pro
                245                 250                 255
Val Ser Gly Leu Gln Val Cys Ser Asn Asp Gln Trp Tyr Ser Ile Pro
            260                 265                 270
Pro Asn Pro Glu Ala Phe Val Ile Asn Ile Gly Asp Thr Phe Thr Ser
        275                 280                 285
Leu Thr Asn Gly Ile Tyr Lys Gly Cys Ile His Arg Ala Val Val Asn
290                 295                 300
Ser Met Asn Ala Arg Lys Ser Leu Ala Phe Phe Leu Cys Pro Ser His
305                 310                 315                 320
Asp Lys Val Val Arg Ala Pro Glu Glu Leu Val Glu Lys Ser Pro Pro
                325                 330                 335
Arg Lys Tyr Pro Asp Tyr Lys Trp Pro Met Leu Leu Glu Met Thr Gln
            340                 345                 350
Lys Arg Tyr Arg Pro Asp Cys Asn Thr Leu Glu Ala Phe Lys Thr Trp
        355                 360                 365
Val Gln Glu Gly Lys Ala Leu Asp Thr Gly Ser Thr Ile Thr Ala Pro
        370                 375                 380
Ser Ala
385

(2) INFORMATION FOR SEQ ID NO: 3:

(i) SEQUENCE CHARACTERISTICS:
        (A) LENGTH: 1259 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iii) ANTI-SENSE: NO (vi) ORIGINAL SOURCE:
        (A) ORGANISM: Arabidopsis thaliana (vii) IMMEDIATE SOURCE:
        (B) CLONE: pAt2301
```

(xi) SEQUENCE DESCRIPTION: SEQ ID NO: 3:

```
AATCTCTCAA AATGGCCGTA AGTTTCGTAA CAACATCTCC TGAGGAAGAA GACAAACCGA      60
AGCTAGGCCT TGGAAATATT CAAACTCCGT TAATCTTCAA CCCTTCAATG CTTAACCTTC     120
AAGCCAATAT CCCAAACCAA TTCATCTGGC CTGACGACGA AAAACCTTCC ATCAACGTTC     180
TCGAGCTTGA TGTTCCTCTC ATCGACCTTC AAAACCTTCT CTCTGATCCA TCCTCCACTT     240
TAGATGCTTC GAGACTGATC TCTGAGGCCT GTAAGAAGCA CGGTTTCTTC CTCGTGGTCA     300
ATCACGGCAT CAGCGAGGAG CTTATATCAG ACGCTCATGA ATACACGAGC CGCTTCTTTG     360
ATATGCCTCT CTCCGAAAAA CAGAGGGTTC TTAGAAAATC CGGTGAGAGT GTTGGCTACG     420
CAAGCAGTTT CACCGGACGC TTCTCCACCA AGCTTCCATG GAAGGAGACC CTTTCTTTCC     480
GGTTTTGCGA CGACATGAGC CGCTCAAAAT CCGTTCAAGA TTACTTCTGC GATGCGTTGG     540
GACATGGGTT TCAGCCATTT GGGAAGGTGT ATCAAGAGTA TTGTGAAGCA ATGAGTTCTC     600
TATCATTGAA GATCATGGAG CTTCTCGGGC TAAGTTTAGG CGTAAAACGG GACTACTTTA     660
GAGAGTTTTT CGAAGAAAAC GATTCAATAA TGAGACTGAA TTACTACCCT CCATGTATAA     720
AACCAGATCT CACACTAGGA ACAGGACCTC ATTGTGATCA ACATCTCTT ACCATCCTTC      780
ACCAAGACCA TGTTAATGGC CTTCAAGTCT TTGTGGAAAA TCAATGGCGC TCCATTCGTC     840
CCAACCCCAA GGCCTTTGTG GTCAATATCG GCGATACTTT CATGGCTCTA TCGAACGATA     900
GATACAAGAG CTGCTTGCAC CGGGCGGTGG TGAACAGCAA GAGCGAGAGG AAGTCACTTG     960
CATTCTTCTT GTGTCCGAAA AAAGACAGAG TAGTGACGCC ACCGAGAGAG CTTTTGGACA    1020
GCATCACATC AAGAAGATAC CCTGACTTCA CATGGTCTAT GTTCCTTGAG TTCACTCAGA    1080
AACATTATAG AGCAGACATG AACACTCTCC AAGCCTTTTC AGATTGGCTC ACCAAACCCA    1140
TCTAAGAAAT AAAATATTCA TGTCTTGTCT TGTTAGTTAC TAGTATCTTC TTTATATTTC    1200
ATGTATGTAT ATGGTAATAG GCAATAACAC CTTTTAGCAT CTCAAAAAAA AAAAAAAA     1259
```

(2) INFORMATION FOR SEQ ID NO: 4:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: protein (iii) HYPOTHETICAL: NO (iii) ANTI-SENSE: NO (vi) ORIGINAL SOURCE:
        (A) ORGANISM: Arabidopsis thaliana (vii) IMMEDIATE SOURCE:
        (B) CLONE: zu Clone pAT2301

(xi) SEQUENCE DESCRIPTION: SEQ ID NO: 4:

```
Met Ala Ser Phe Val Thr Thr Ser Pro Glu Glu Asp Lys Pro
 1               5                  10                  15

Lys Leu Gly Leu Gly Asn Ile Gln Thr Pro Leu Ile Phe Asn Pro Ser
            20                  25                  30

Met Leu Asn Leu Gln Ala Asn Ile Pro Asn Gln Phe Ile Trp Pro Asp
        35                  40                  45

Asp Glu Lys Pro Ser Ile Asn Val Leu Glu Leu Asp Val Pro Leu Ile
    50                  55                  60

Asp Leu Gln Asn Leu Leu Ser Asp Pro Ser Ser Thr Leu Asp Ala Ser
```

```
            65                  70                  75                  80
Arg Leu Ile Ser Glu Ala Cys Lys Lys His Gly Phe Phe Leu Val Val
                    85                  90                  95

Asn His Gly Ile Ser Glu Glu Leu Ile Ser Asp Ala His Glu Tyr Thr
                100                 105                 110

Ser Arg Phe Phe Asp Met Pro Leu Ser Glu Lys Gln Arg Val Leu Arg
            115                 120                 125

Lys Ser Gly Glu Ser Val Gly Tyr Ala Ser Ser Phe Thr Gly Arg Phe
        130                 135                 140

Ser Thr Lys Leu Pro Trp Lys Glu Thr Leu Ser Phe Arg Phe Cys Asp
145                 150                 155                 160

Asp Met Ser Arg Ser Lys Ser Val Gln Asp Tyr Phe Cys Asp Ala Leu
                165                 170                 175

Gly His Gly Phe Gln Pro Phe Gly Lys Val Tyr Gln Glu Tyr Cys Glu
            180                 185                 190

Ala Met Ser Ser Leu Ser Leu Lys Ile Met Glu Leu Leu Gly Leu Ser
        195                 200                 205

Leu Gly Val Lys Arg Asp Tyr Phe Arg Glu Phe Phe Glu Glu Asn Asp
    210                 215                 220

Ser Ile Met Arg Leu Asn Tyr Tyr Pro Pro Cys Ile Lys Pro Asp Leu
225                 230                 235                 240

Thr Leu Gly Thr Gly Pro His Cys Asp Pro Thr Ser Leu Thr Ile Leu
                245                 250                 255

His Gln Asp His Val Asn Gly Leu Gln Val Phe Val Glu Asn Gln Trp
            260                 265                 270

Arg Ser Ile Arg Pro Asn Pro Lys Ala Phe Val Val Asn Ile Gly Asp
        275                 280                 285

Thr Phe Met Ala Leu Ser Asn Asp Arg Tyr Lys Ser Cys Leu His Arg
290                 295                 300

Ala Val Val Asn Ser Lys Ser Glu Arg Lys Ser Leu Ala Phe Phe Leu
                310                 315                 320
305

Cys Pro Lys Lys Asp Arg Val Val Thr Pro Arg Glu Leu Leu Asp
            325                 330                 335

Ser Ile Thr Ser Arg Arg Tyr Pro Asp Phe Thr Trp Ser Met Phe Leu
        340                 345                 350

Glu Phe Thr Gln Lys His Tyr Arg Ala Asp Met Asn Thr Leu Gln Ala
    355                 360                 365

Phe Ser Asp Trp Leu Thr Lys Pro Ile
370                 375

(2) INFORMATION FOR SEQ ID NO: 5:

(i) SEQUENCE CHARACTERISTICS:
        (A) LENGTH: 1490 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iii) ANTI-SENSE: NO (vi) ORIGINAL SOURCE:
        (A) ORGANISM: Arabidopsis thaliana (vii) IMMEDIATE SOURCE:
        (B) CLONE: pAT2353
```

(xi) SEQUENCE DESCRIPTION: SEQ ID NO: 5:

```
GGTATCGATA AGCTTGATAT CGAATTCGAG GATCCGGGAC CATGGACAAA AACCCCAAAA        60

CTCTCAAGAA AAAAAAAGA AAAGAAATGG CGATACTATG CACAACAACA TCTCCGGCAG       120

AGAAAGAACA CGAACCAAAA CAAGATCTTG AAAAAGACCA AACTTCTCCA CTAATCTTTA       180

ACCCTTCTCT TCTTAACCTC CAATCCCAAA TCCCAAACCA ATTCATTTGG CCAGACGAAG       240

AGAAACCTTC CATTGACATT CCAGAGCTCA ACGTCCCGTT CATCGATCTC TCAAGCCAAG       300

ACTCGACTCT TGAAGCTCCT AGAGTCATCG CAGAAGCTTG CACCAAACAC GGCTTCTTCC       360

TCGTCGTCAA TCATGGCGTC AGCGAGTCAC TAATAGCGGA TGCTCACCGT TTGATGGAAA       420

GTTTCTTCGA CATGCCTCTC GCCGGCAAAC AGAAAGCTCA GAGAAAACCC GGTGAGAGTT       480

GTGGCTATGC AAGTAGCTTC ACCGGCAGAT TCTCCACTAA GCTGCCATGG AAGGAGACTC       540

TCTCTTTTCA GTTTTCCAAC GATAATAGTG GCTCGAGAAC CGTTCAAGAT TACTTTTCCG       600

ATACATTAGG ACAAGAGTTC GAGCAGTTTG GGAAGGTGTA TCAAGACTAT TGTGAAGCAA       660

TGAGTTCTCT ATCACTCAAG ATCATGGAGC TTCTGGGCTT AAGTTTAGGC GTAAACCGAG       720

ACTATTTCCG AGGATTTTTC GAAGAGAACG ATTCGATAAT GAGGCTCAAT CATTATCCTC       780

CATGCCAAAC ACCAGATCTC ACGTTAGGTA CAGGACCTCA TTGTGATCCA AGTTCTTTGA       840

CCATCCTTCA TCAAGACCAT GTCAATGGCC TTCAAGTCTT TGTCGACAAT CAATGGCAAT       900

CCATTCGTCC CAATCCCAAG GCTTTCGTTG TCAATATTGG TGACACTTTC ATGGCTCTAT       960

CGAACGGGAT ATTCAAGAGC TGTTTGCATA GAGCGGTTGT GAATAGAGAG AGCGCGAGAA      1020

AATCGATGGC GTTTTTCTTG TGTCCGAAGA AGACAAAGT GGTGAAACCA CCAAGTGATA      1080

TTTTGGAGAA GATGAAAACA AGAAAATACC CTGACTTCAC TTGGTCTATG TTCCTTGAGT      1140

TCACTCAAAA ACATTACCGA GCAGATGTGA ATACTCTCGA TTCCTTTTCT AATTGGGTTA      1200

TTACCAACAA CAATCCCATC TAAGAAACAA AATTATTTAC TATCTCAATC TTTTGTTTTT      1260

CTTTGGTTAC TTTGTGTCCT TGTTCTCAT GGTGAAATGC ATTAAATTGC ATTTCAAAGT      1320

TTTAAACGTT TGTATATTGA TTGTTCCAAG CTTTAGACCA ATCCCTACCG TATGAGCTCG      1380

TTCAATGAAT AATTTGAATG AAAAATTCAA AGAAATTTTT CTTAAAAAAA AAAAAAAAA      1440

AAAAAAAAAA AAAAAAAAA AAAAAAAAA CCATGGTACC CGGATCCTCG      1490
```

(2) INFORMATION FOR SEQ ID NO: 6:

(i) SEQUENCE CHARACTERISTICS:
        (A) LENGTH: 378 amino acids
        (B) TYPE: amino acid
        (C) STRANDEDNESS: single
        (D) TOPOLOGY: linear (ii) MOLECULE TYPE: protein (iii) HYPOTHETICAL: NO (iii) ANTI-SENSE: NO (vi) ORIGINAL SOURCE:
        (A) ORGANISM: Arabidopsis thaliana (vii) IMMEDIATE SOURCE:
        (B) CLONE: zu pAT2353

(xi) SEQUENCE DESCRIPTION: SEQ ID NO: 6:

```
Met Ala Ile Leu Cys Thr Thr Thr Ser Pro Ala Glu Lys Glu His Glu
 1               5                  10                  15

Pro Lys Gln Asp Leu Glu Lys Asp Gln Thr Ser Pro Leu Ile Phe Asn
            20                  25                  30
```

```
Pro Ser Leu Leu Asn Leu Gln Ser Gln Ile Pro Asn Gln Phe Ile Trp
        35                  40                  45
Pro Asp Glu Glu Lys Pro Ser Ile Asp Ile Pro Glu Leu Asn Val Pro
        50                  55                  60
Phe Ile Asp Leu Ser Ser Gln Asp Ser Thr Leu Glu Ala Pro Arg Val
65                  70                  75                  80
Ile Ala Glu Ala Cys Thr Lys His Gly Phe Phe Leu Val Val Asn His
                85                  90                  95
Gly Val Ser Glu Ser Leu Ile Ala Asp Ala His Arg Leu Met Glu Ser
                100                 105                 110
Phe Phe Asp Met Pro Leu Ala Gly Lys Gln Lys Ala Gln Arg Lys Pro
        115                 120                 125
Gly Glu Ser Cys Gly Tyr Ala Ser Ser Phe Thr Gly Arg Phe Ser Thr
        130                 135                 140
Lys Leu Pro Trp Lys Glu Thr Leu Ser Phe Gln Phe Ser Asn Asp Asn
145                 150                 155                 160
Ser Gly Ser Arg Thr Val Gln Asp Tyr Phe Ser Asp Thr Leu Gly Gln
                165                 170                 175
Glu Phe Glu Gln Phe Gly Lys Val Tyr Gln Asp Tyr Cys Glu Ala Met
                180                 185                 190
Ser Ser Leu Ser Leu Lys Ile Met Glu Leu Leu Gly Leu Ser Leu Gly
        195                 200                 205
Val Asn Arg Asp Tyr Phe Arg Gly Phe Phe Glu Glu Asn Asp Ser Ile
        210                 215                 220
Met Arg Leu Asn His Tyr Pro Pro Cys Gln Thr Pro Asp Leu Thr Leu
225                 230                 235                 240
Gly Thr Gly Pro His Cys Asp Pro Ser Ser Leu Thr Ile Leu His Gln
                245                 250                 255
Asp His Val Asn Gly Leu Gln Val Phe Val Asp Asn Gln Trp Gln Ser
                260                 265                 270
Ile Arg Pro Asn Pro Lys Ala Phe Val Val Asn Ile Gly Asp Thr Phe
        275                 280                 285
Met Ala Leu Ser Asn Gly Ile Phe Lys Ser Cys Leu His Arg Ala Val
        290                 295                 300
Val Asn Arg Glu Ser Ala Arg Lys Ser Met Ala Phe Phe Leu Cys Pro
305                 310                 315                 320
Lys Lys Asp Lys Val Val Lys Pro Pro Ser Asp Ile Leu Glu Lys Met
                325                 330                 335
Lys Thr Arg Lys Tyr Pro Asp Phe Thr Trp Ser Met Phe Leu Glu Phe
                340                 345                 350
Thr Gln Lys His Tyr Arg Ala Asp Val Asn Thr Leu Asp Ser Phe Ser
        355                 360                 365
Asn Trp Val Ile Thr Asn Asn Pro Ile
370                 375
```

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO

```
        (iii) ANTI-SENSE: NO (v) FRAGMENT TYPE: internal (vi) ORIGINAL SOURCE:
             (A) ORGANISM: Cucurbita maxima
             (F) TISSUE TYPE: Endosperm (xi) SEQUENCE DESCRIPTION: SEQ ID NO: 7:

Val Phe Gly Gly Ser Asp Glu Ser Lys
 1               5

(2) INFORMATION FOR SEQ ID NO: 8:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (iii) HYPOTHETICAL: NO (iii) ANTI-SENSE: NO (v) FRAGMENT TYPE: internal (vii) IMMEDIATE SOURCE:
             (B) CLONE: zu Primer 1 (Beispiel 38)

(xi) SEQUENCE DESCRIPTION: SEQ ID NO: 8:

Asn Tyr Tyr Pro Thr Cys
 1               5

(2) INFORMATION FOR SEQ ID NO: 9:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (iii) HYPOTHETICAL: NO (v) FRAGMENT TYPE: internal (vii) IMMEDIATE SOURCE:
             (B) CLONE: zu Primer 2 (Beispiel 38)

(xi) SEQUENCE DESCRIPTION: SEQ ID NO: 9:

Phe Val Ile Asn Ile Gly Asp
 1               5

(2) INFORMATION FOR SEQ ID NO: 10:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
             (B) CLONE: Primer 1 (Beispiel 38)

(xi) SEQUENCE DESCRIPTION: SEQ ID NO: 10:
```

```
GCAAGCTTAA YTAYTAYCCN ACNTG                                                     25
```

(2) INFORMATION FOR SEQ ID NO: 11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: Primer 2 (Beispiel 38)

(xi) SEQUENCE DESCRIPTION: SEQ ID NO: 11:

```
AARCANTADT TRTADCCNCT TAAGCG                                                    26
```

(2) INFORMATION FOR SEQ ID NO: 12:

(i) SEQUENCE CHARACTERISTICS:
        (A) LENGTH: 174 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Arabidopsis thaliana (vii) IMMEDIATE SOURCE:
        (B) CLONE: pAt2204

(xi) SEQUENCE DESCRIPTION: SEQ ID NO: 12:

```
AATTACTACC CTACGTGTAT AAAACCAGAT CTCACACTAG GAACAGGACC TCATTGTGAT                60

CCAACATCTC TTACCATCCT TCACCAAGAC CATGTTAATG GCCTTCAAGT CTTTGTGGAA               120

AATCAATGGC GCTCCATTCG TCCCAACCCC AAGGCCTTTG TAATTAACAT CGGA                    174
```

(2) INFORMATION FOR SEQ ID NO: 13:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: internal (vi) ORIGINAL SOURCE:
        (A) ORGANISM: Arabidopsis thaliana (vii) IMMEDIATE SOURCE:
        (B) CLONE: zu Clone pAt2204

(xi) SEQUENCE DESCRIPTION: SEQ ID NO: 13:

Asn Tyr Tyr Pro Thr Cys Ile Lys Pro Asp Leu Thr Leu Gly Thr Gly

```
         1               5              10              15

Pro His Cys Asp Pro Thr Ser Leu Thr Ile Leu His Gln Asp His Val
            20                  25                  30

Asn Gly Leu Gln Val Phe Val Glu Asn Gln Trp Arg Ser Ile Arg Pro
        35                  40                  45

Asn Pro Lys Ala Phe Val Ile Asn Ile Gly
    50                  55
```

(2) INFORMATION FOR SEQ ID NO: 14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: Oligo (Beispiel 39a)

(xi) SEQUENCE DESCRIPTION: SEQ ID NO: 14:

GAGAATTCTA AGTTGATAAT GGTTATTG                          28

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: Oligo 1 (Beispiel 39b)

(xi) SEQUENCE DESCRIPTION: SEQ ID NO: 15:

GAGAATTCAA AATGGCCGTA AGTTTCG                           27

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
        (B) CLONE: Oligo 2 (Beispiel 39b)

(xi) SEQUENCE DESCRIPTION: SEQ ID NO: 16:

GAGAATTCAG AAATGGCGAT ACTATGC                           27

(2) INFORMATION FOR SEQ ID NO: 17:

```
        (i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (vii) IMMEDIATE SOURCE:
            (B) CLONE: Oligo 3   (Beispiel 39b)

(xi) SEQUENCE DESCRIPTION: SEQ ID NO: 17:

GAGAATTCAA AAATGGCAAC GGAATGC                                               27

(2) INFORMATION FOR SEQ ID NO: 18:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 18:

AATTCGAACC CCTTCG                                                           16

(2) INFORMATION FOR SEQ ID NO: 19:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 19:

GATCCGAAGG GGTTCG                                                           16
```